(12) United States Patent
Song

(10) Patent No.: US 7,144,865 B2
(45) Date of Patent: Dec. 5, 2006

(54) COMPOSITIONS AND METHODS FOR TREATING OBESITY

(75) Inventor: Moon K. Song, Northridge, CA (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 303 days.

(21) Appl. No.: 10/768,200

(22) Filed: Jan. 30, 2004

(65) Prior Publication Data

US 2004/0185125 A1 Sep. 23, 2004

Related U.S. Application Data

(60) Provisional application No. 60/444,605, filed on Jan. 31, 2003.

(51) Int. Cl.
*A61K 38/00* (2006.01)
*A61K 36/48* (2006.01)
*A61K 31/13* (2006.01)

(52) U.S. Cl. .................. 514/19; 424/757; 424/641

(58) Field of Classification Search .............. None
See application file for complete search history.

(56) References Cited

U.S. PATENT DOCUMENTS

| | | | |
|---|---|---|---|
| 4,273,763 A * | 6/1981 | Horrobin | 424/642 |
| 5,411,748 A | 5/1995 | Song | |
| 5,418,218 A | 5/1995 | Wilber | |
| 5,834,032 A | 11/1998 | Song | |
| 5,904,926 A * | 5/1999 | Slavin | 424/401 |
| 5,989,574 A | 11/1999 | Slavin | |
| 5,997,908 A | 12/1999 | Song | |

OTHER PUBLICATIONS

Russo et al. Hypertension. 1997. vol. 29, No. 4, pp. 1058-1063, MEDLINE Abstract enclosed.*
Eder et al. J. Nutritional Biochem. 1997. vol. 8, No. 8, pp. 461-468, EMBASE Abstract enclosed.*

*Effect of arachidonic acid plus zinc on glucose disposal in genetically diabetic (ob/ob) mice*, I.K. Hwang et al., *Diabetes, Obesity and Metabolism*, Apr. 2002, pp. 124-131.
*Antidiabetic Actions of Arachidonic Acid and Zinc in Genetically Diabetic Goto-Kakizaki Rats*, Moon K. Song et al., *Metabolism*, vol. 52, No. 1 (Jan.), 2003; pp. 7-12.
*Synergistic Antidiabetic Activities of Zinc, Cyclo (His-Pro), and Arachidonic Acid*, Moon K. Song et al., *Metabolism*, vol. 50, No. 1 (Jan.), 2001; pp. 53-59.
*Animal Prostate Extract Ameliorates Diabetic Symptoms by Stimulating Intestinal Zinc Absorption in Rats*, M.K. Song et al., *Diabetes Research*(1996), 31: pp. 157-170.
*Metabolism of Glucose by Rat Pancreatic Islets and Kidney: Comparison of Membrane Preparations with Intact Tissue*, Moon K. Song et al., *Pancreas*, vol. 24, No. 2, 2002, pp. 205-209.
*Effects of Bovine Prostate Powder on Zinc, Glucose, and Insulin Metabolism in Old Patients with Non-Insulin-Dependent Diabetes Mellitus*, M.K. Song et al., *Metabolism*, vol. 47, No. 1 (Jan. ), 1998, pp. 39-43.
*Effects of arachidonic acid and cyclo (his-pro) on zinc transport across small intestine and muscle tissues*; M.J. Rosenthal et al., *Life Sciences* 70 (2001) 337-348.
*Anti-Hyperglycemic Activity of Zinc Plus Cyclo (His-Pro) in Genetically Diabetic Goto-Kakizaki and Aged Rats*, Moon K. Song et al., *Control of Diabetes by Cyclo (His-Pro)*, pp. 1338-1345, 2003.
*Effects of cyclo (his-pro) plus zinc on glucose metabolism in genetically diabetic obese mice*, I.K. Hwang et al., *Diabetes, Obesity and Metabolism*, May 2003, pp. 317-324.

* cited by examiner

*Primary Examiner*—Christopher R. Tate
(74) *Attorney, Agent, or Firm*—Knobbe Martens Olson & Bear LLP

(57) ABSTRACT

The present invention relates to dietary supplementing methods useful for controlling obesity. More particularly, the invention relates to methods of administration of compositions containing defined chemical species useful for prevention and treatment of obesity. In a preferred embodiment, pharmaceutical compositions used in connection with the present invention comprise: (1) a zinc salt, (2) cyclo-Hispro and/or (3) arachidonic acid, and (4) at least one pharmaceutically acceptable excipient. More particularly, the invention relates to methods of manufacturing of preparing a soybean protein hydrolysate (SPH) comprising cyclo-Hispro.

24 Claims, 13 Drawing Sheets

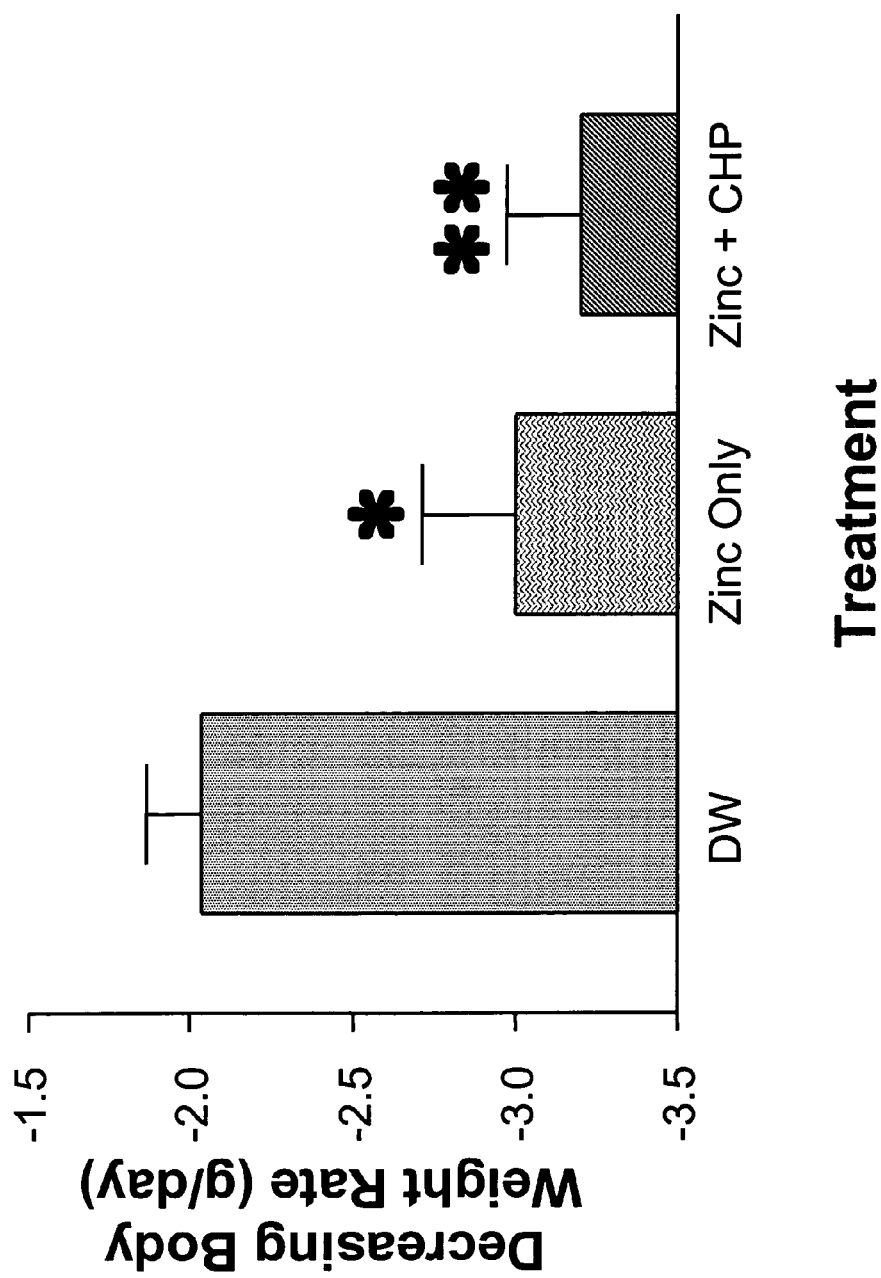
Fig. 1 Effects of CHP treatment on body weight changes in G-K rats (10 month old). Values are mean +/- SEM *p<0.05 and **p<0.01 compared to controls

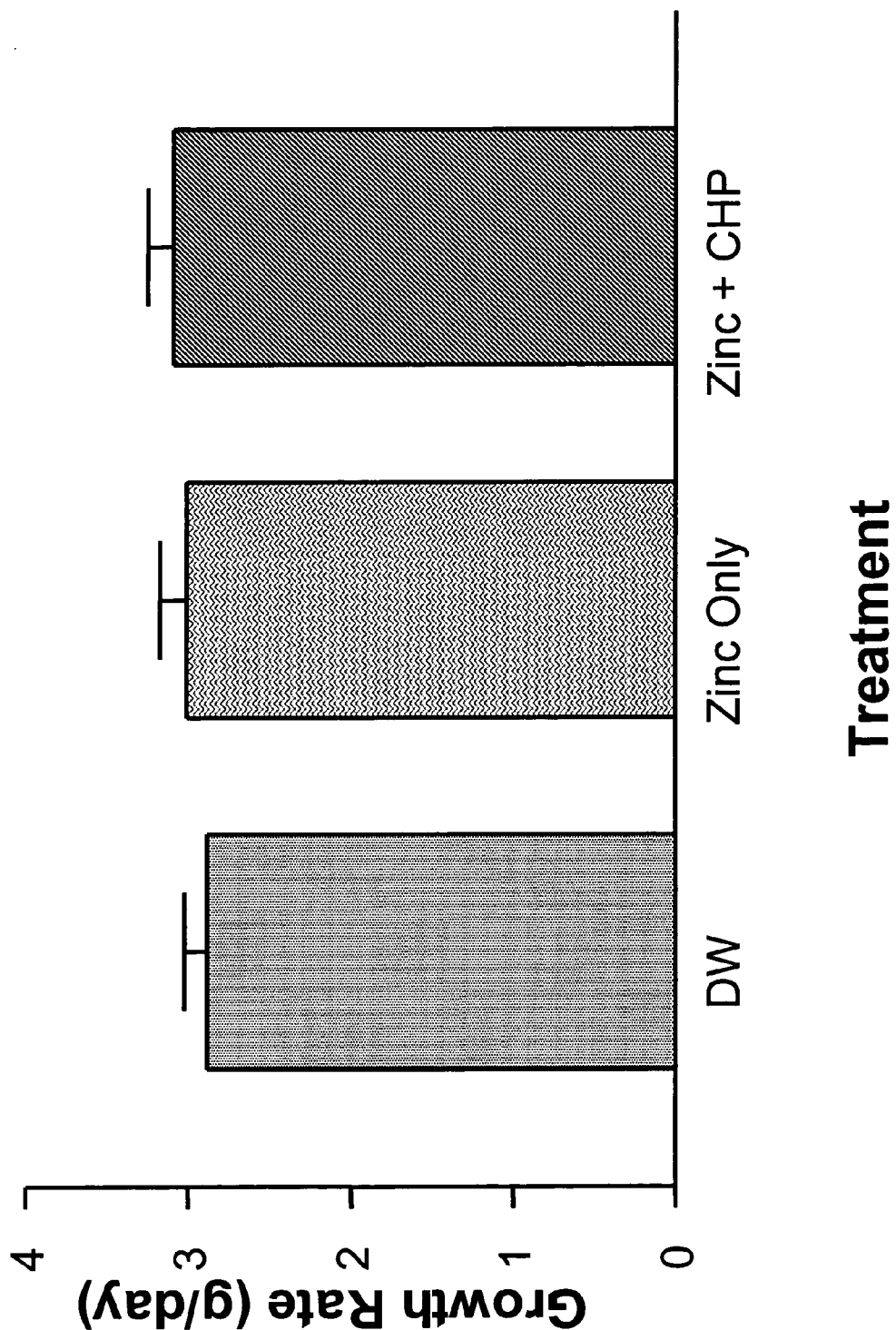
Fig. 2 Effects of CHP treatment on body weight gain in young (1 month-old) G-K rats

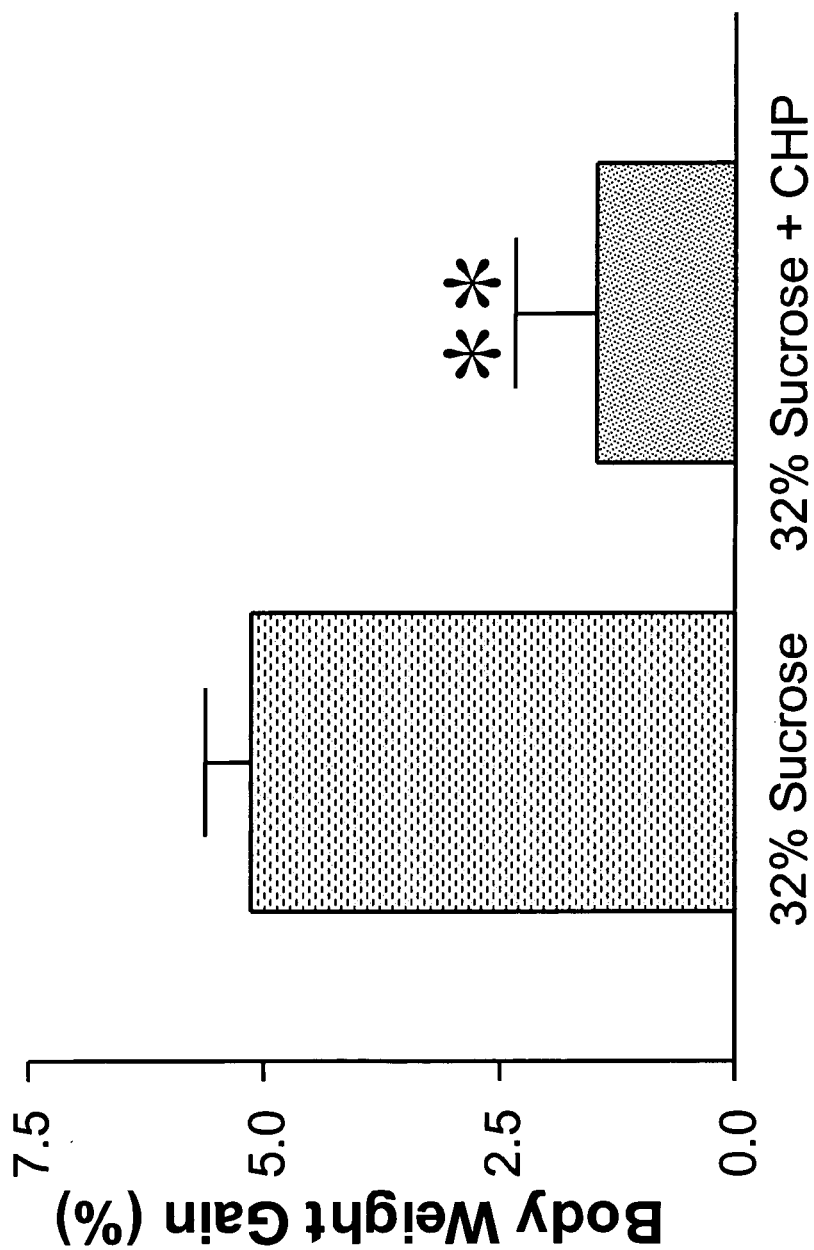
Fig. 3 Effects of CHP treatment on body weight gain in C57BL/6J mice (8 month old) **p<0.01 vs. Controls (32% sucrose)

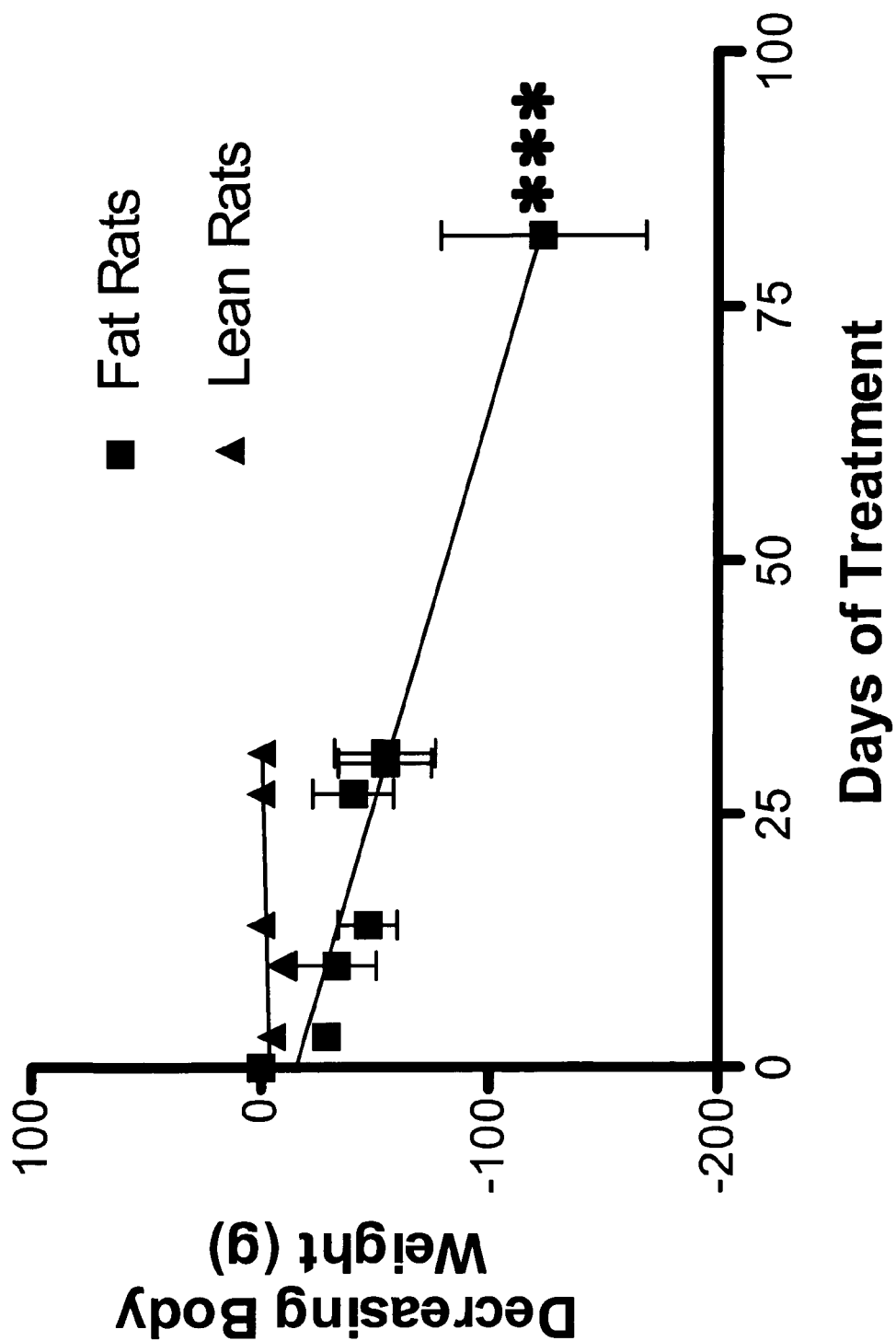
Fig.4 Effects of zinc plus CHP on body weight change in aged fatty obese S-D rats. ***p<0.001 compared to lean rats.

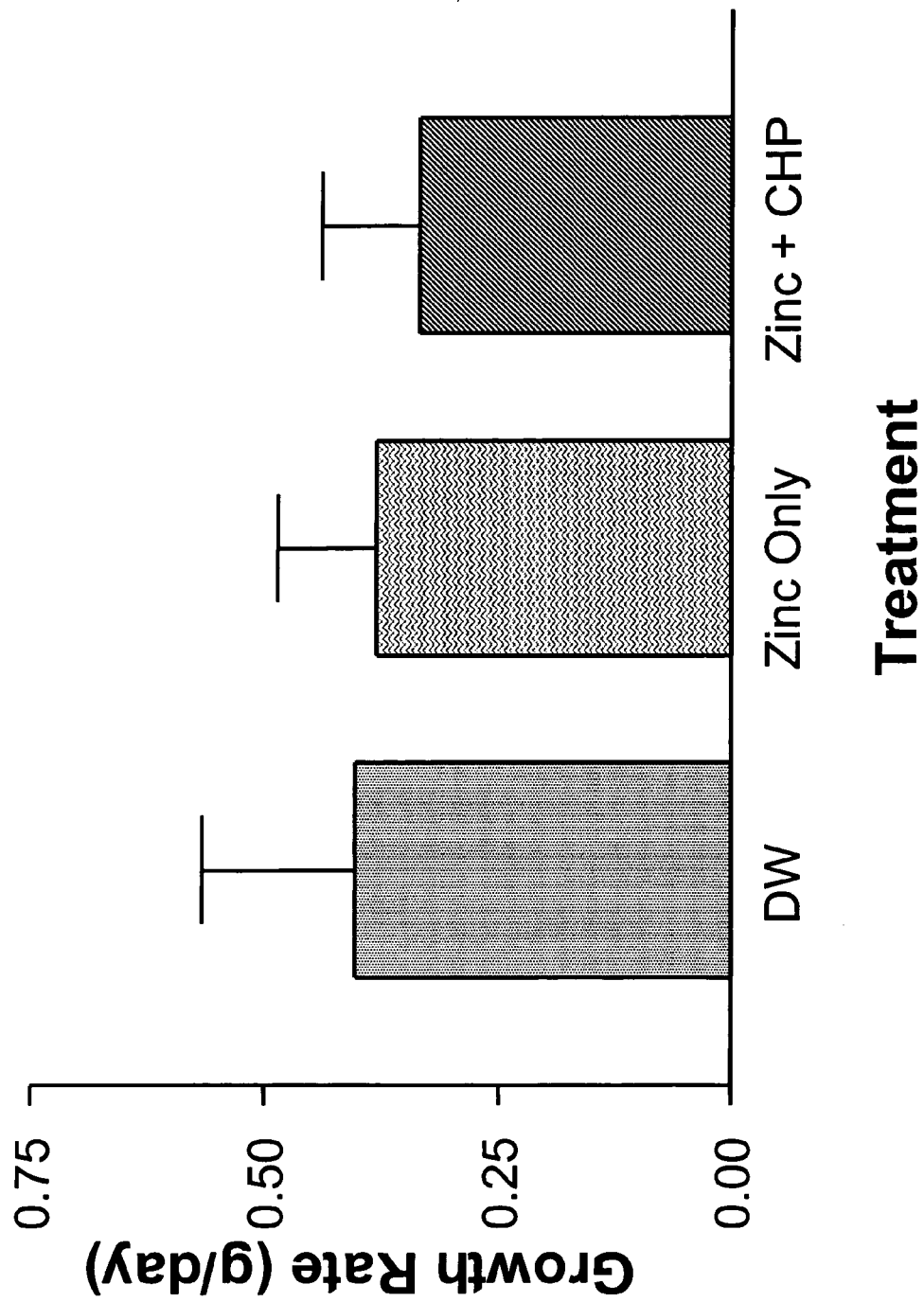
Fig. 5 Effects of zinc plus CHP on body weight change in aged normal weight S-D rats.

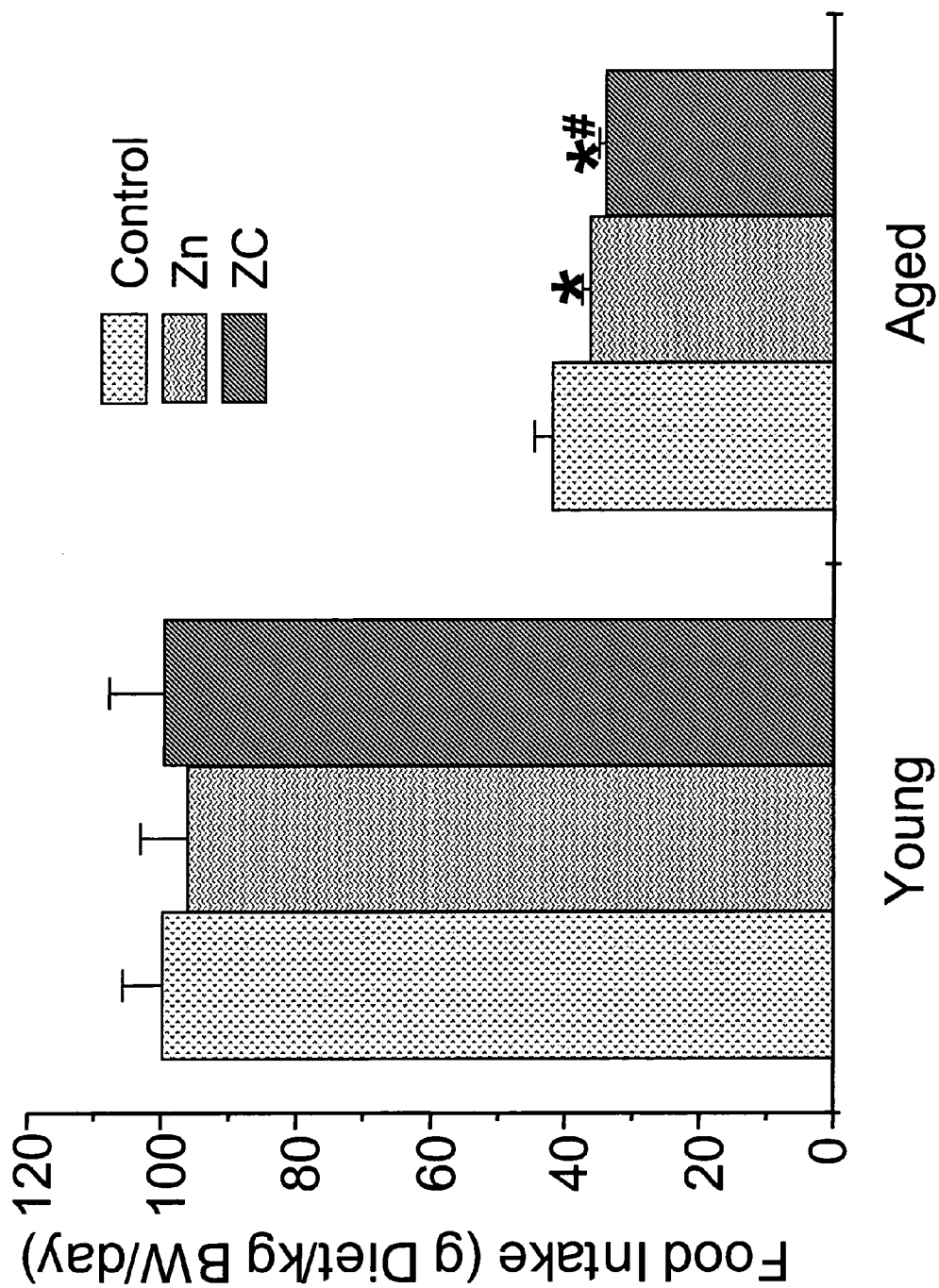
Fig. 6 Effects of zinc or zinc plus CHP treatment on food intake in G-K rats. *p<0.05 and *#p<0.01 compared to control.

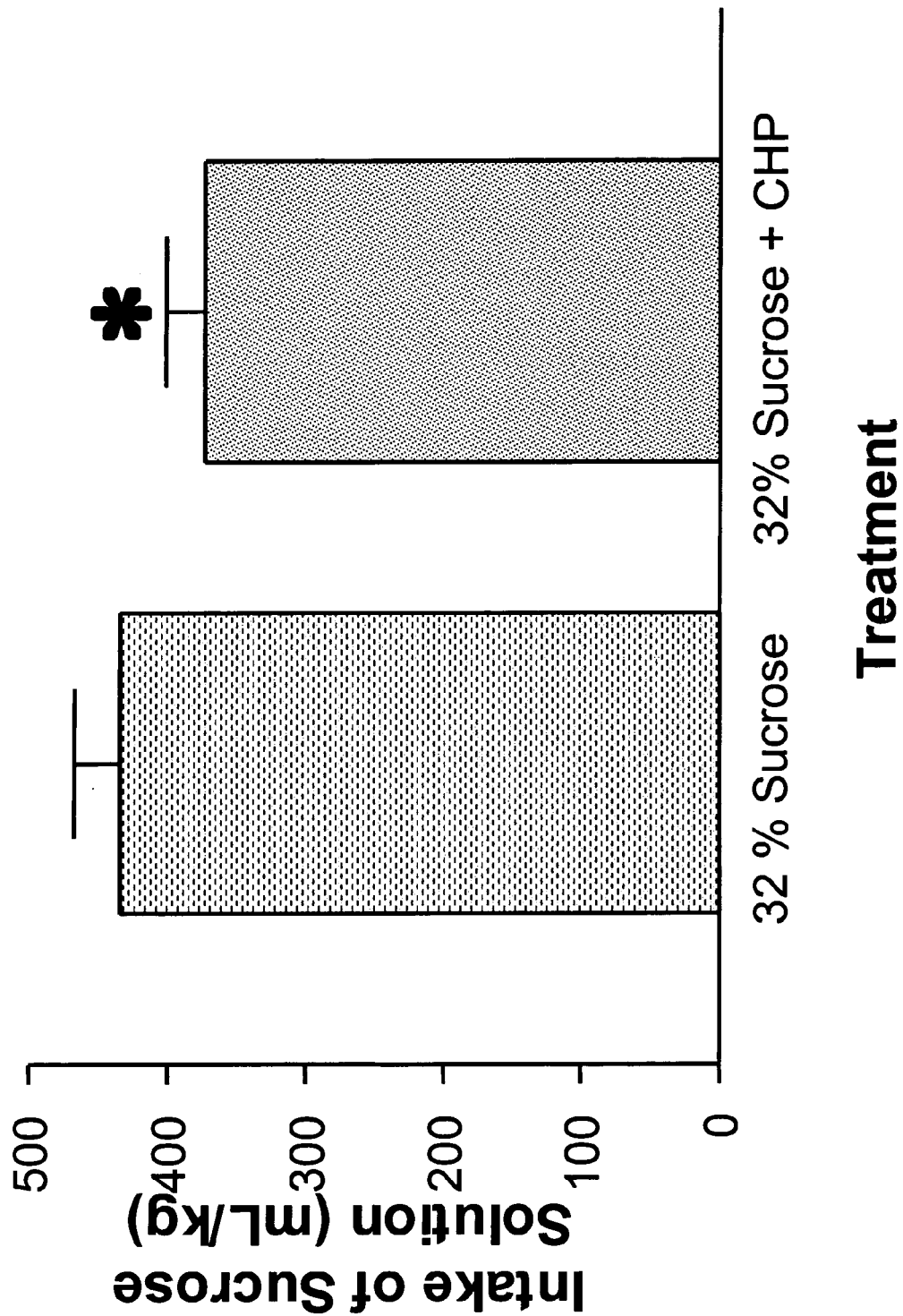
Fig. 7 Effects of zinc plus CHP on sucrose solution intake in C57BL/6J mice. *p<0.05 vs. controls.

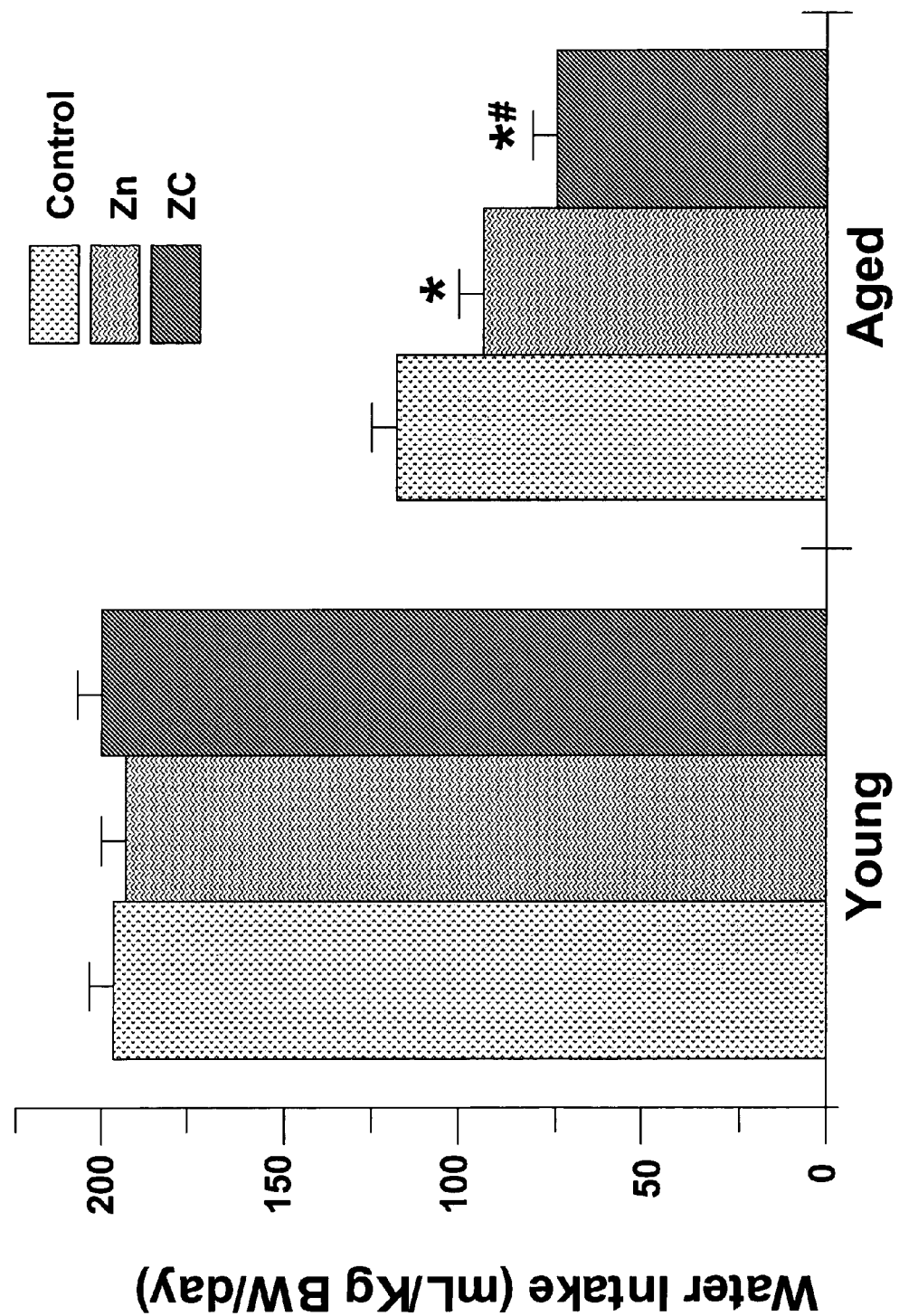
Fig. 8 Effects of zinc or zinc plus CHP treatment on water intake in G-K rats. *$p<0.05$ and *#$<0.01$ compared to control

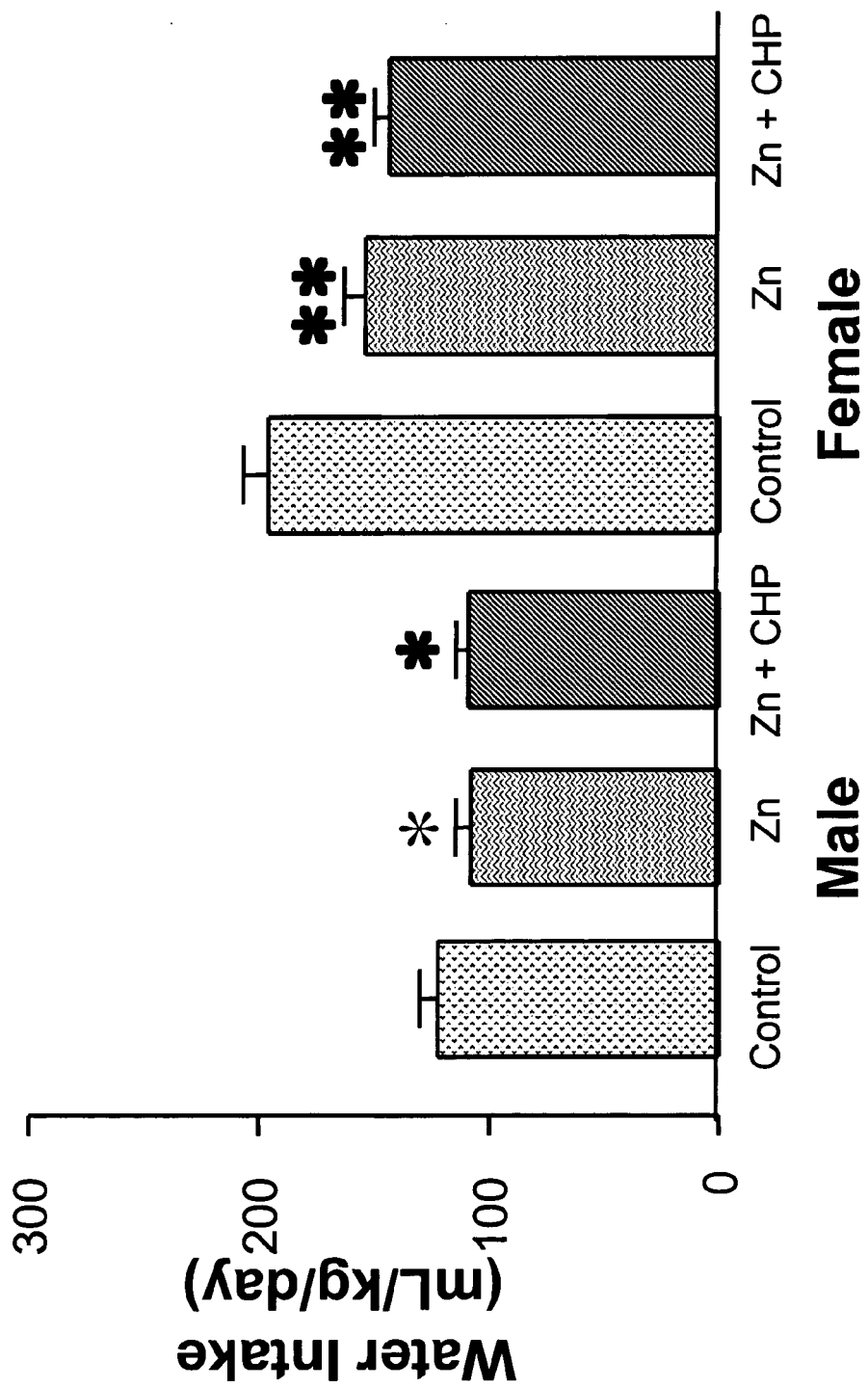
Fig. 9 Effects of zinc or zinc plus CHP treatment on water intake in S-D rats. Values are mean +/- SEM. *p<0.05; **p<0.01

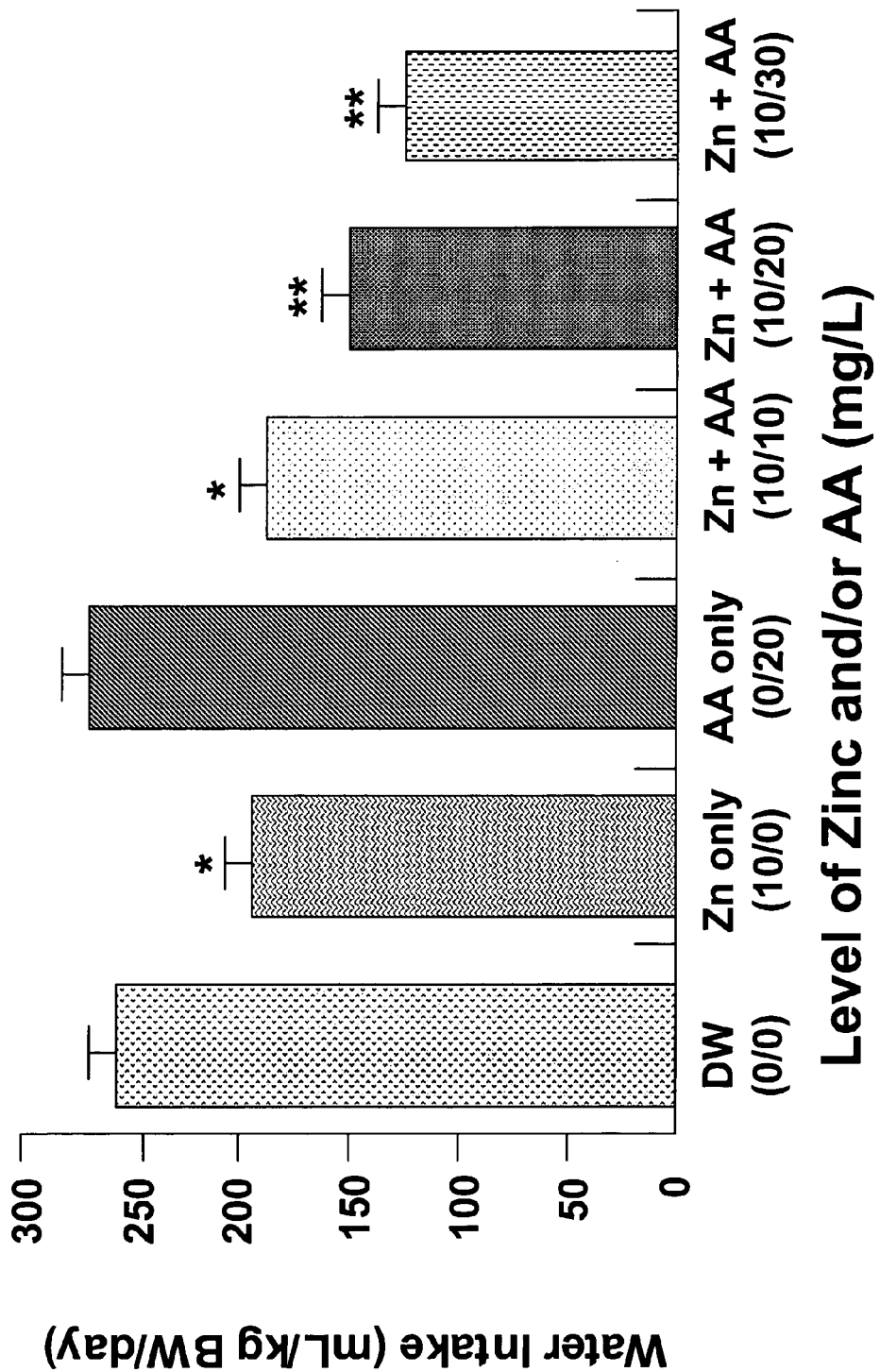
Fig. 10 Effects of zinc or zinc plus various doses of AA treatment on water intake in G-K rats. *$p<0.05$ and **$p<0.01$ compared to controls.

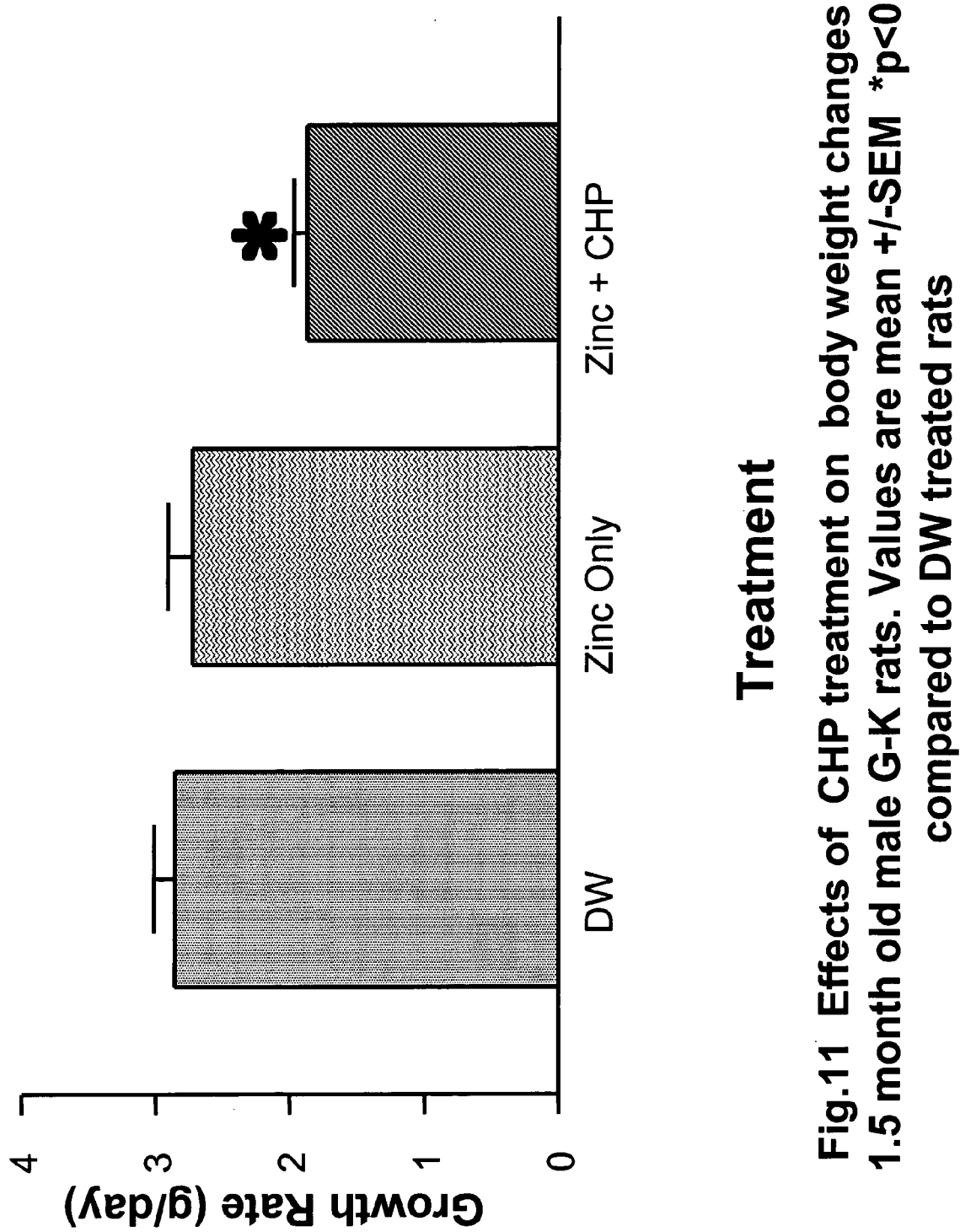
Fig.11 Effects of CHP treatment on body weight changes in 1.5 month old male G-K rats. Values are mean +/-SEM *$p<0.05$ compared to DW treated rats

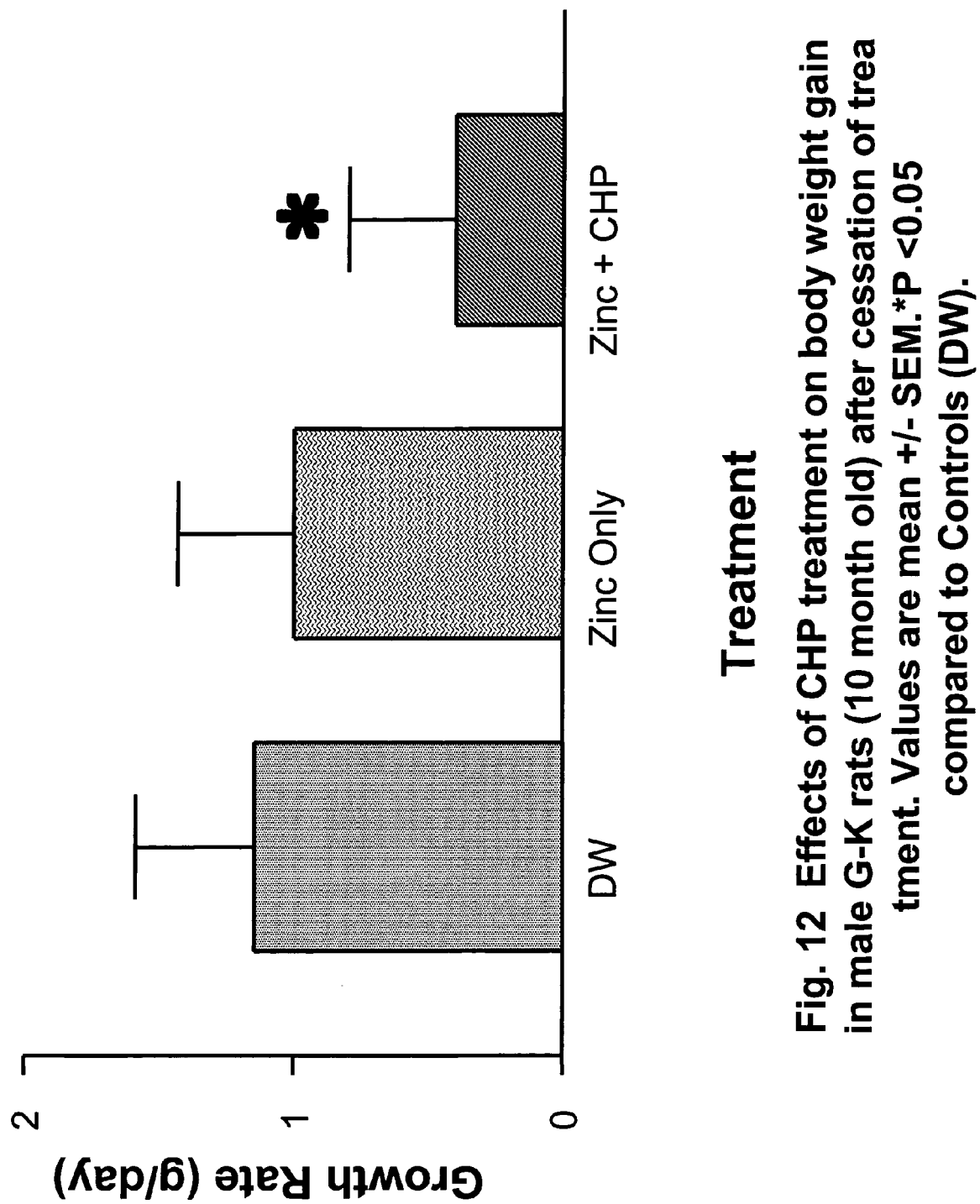
Fig. 12 Effects of CHP treatment on body weight gain in male G-K rats (10 month old) after cessation of treatment. Values are mean +/- SEM.*P <0.05 compared to Controls (DW).

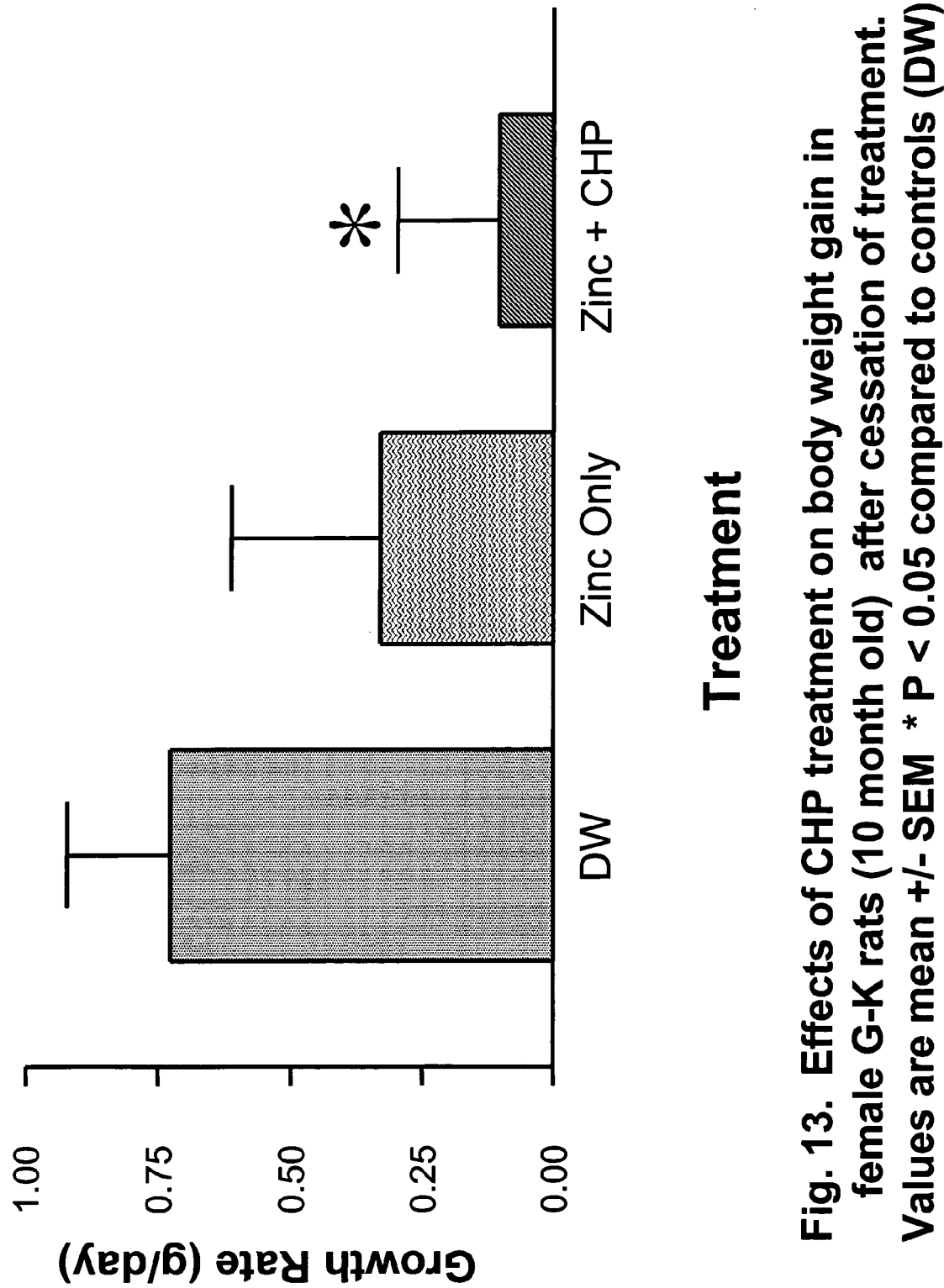
Fig. 13. Effects of CHP treatment on body weight gain in female G-K rats (10 month old) after cessation of treatment. Values are mean +/- SEM  * P < 0.05 compared to controls (DW)

COMPOSITIONS AND METHODS FOR TREATING OBESITY

RELATED APPLICATION DATA

This application claims priority under 35 U.S.C. 119(e) to Provisional Application No. 60/444,605 filed Jan. 31, 2003. The disclosure of this provisional application is incorporated in its entirety herein by reference.

FIELD OF THE INVENTION

The present invention relates to dietary supplementing methods useful for controlling obesity. More particularly, the invention relates to methods of administration of compositions containing defined chemical species useful for prevention and treatment of obesity. More particularly, the invention relates to methods of manufacturing one chemical species within said composition.

BACKGROUND OF THE INVENTION

Obesity is now a world wide epidemic, and is one of the most serious contributors to increased morbidity and mortality. Obesity is prevalent in the United States, affecting more than 61% of the total population. One out of every three Americans is afflicted with obesity and another one third are overweight (Flegal, et al., *Overweight and Obesity in the United States: Prevalence and Trends, 1960–1994*. Int J Obes 22:39–47, 1998). Obesity is defined by the United States Centers for Disease Control and Prevention (CDC) as an excessively high amount of body fat or adipose tissue in relation to lean body mass and overweight as an increased body weight in relation to height, when compared to some standard of acceptable or desirable weight. The CDC alternatively defines overweight as a person with a body mass index (BMI) between 25.0 and 29.9 and obesity is defined as a BMI greater than or equal to 30.0. Obese and overweight mammals suffer from increased joint problems, increased rates of high blood pressure, and high cholesterol. Increased weight is also associated with heart disease, stroke and diabetes. In 1998, consumers spent $33 billion in the United States for weight-loss products and services with very little success (Serdula, et al., *Prevalence of Attempting Weight Loss and Strategies for Controlling Weight*, JAMA 282: 1353–1358, 1999). Thus, obesity and its associated complications continue to be a major problem throughout the worldwide health care system.

Obesity is caused by both genetic and environmental factors. Genetic causes of this abnormality can result from a single gene mutation in animals, such as ob/ob mice, db/db mice, and obese fatty Zucker rats, but humans rarely develop obesity from a single gene mutation (Chaganon, et al., *The Human Obesity Gene Map: The 1997 Update*, Obes Res 6:76–92, 1998). Leptin deficiency from a single gene mutation was identified in ob/ob mice (Zhang, et al., *Positional Cloning of the Mouse Obese Gene and its Human Homologue*, Nature 372:425–432, 1994) and subsequently also in humans (Montague, et al., *Congenital Leptin Deficiency is Associated With Severe Early-Onset Obesity in Human*, Nature 387:903–908, 1997). Leptin deficiency is associated with hyperphagia, hyperinsulinemia, and insulin resistance (Prasad, et al., *A Paradoxical Elevation of Brain Cyclo (his-pro) Levels in Hyperphagic Obese Zucker Rats*, Brain Res 699:149–153, 1995). Administration of leptin reversed all of these symptoms. Leptin is produced exclusively in fat cells and the placenta, and blood-borne leptin signals the brain regarding quantities of stored fat by binding to the receptors in the hypothalamus. Leptin also interacts with the appetite and satiety centers in the brain to regulate body weight by balancing food intake and energy expenditures such as exercise and glucose metabolism (Halaas, et al., *Weight-Reducing Effects of the Plasma Protein Encoded by the Obese Gene*, Science 269:543–546, 1995). Leptin reduces hypothalamic neuropeptide Y (NPY) gene expression. (Schwartz, et al., *Identification of Targets of Leptin Action in Rat Hypothalamus*, J Clin Invest 98:1101–1106, 1996; Levine, et al., *Neuropeptide Y: A Potent Inducer of Consummatory Behavior in Rats*, Peptides 5:1025–1029, 1984). While ob/ob mice are deficient in leptin production, diabetic db/db mice and obese fatty Zucker rats have defective leptin receptor function. However, genetic abnormalities of leptin-receptor malfunction were not identified in human obesity (Considine, et al., *Serum Immunoreactive-Leptin Concentrations in Normal Weight and Obese Humans*, N Engl J Med 334:292–295, 1996). Most human obesity arises from increased food intake and decreased expenditure of energy (Bouchard, et al., *The Response to Long-Term Overfeeding in Identical Twins*, N Engl J Med 322:1477–1482, 1990). The surplus energy is stored as fat in adipose tissues. However, a variety of growth hormones, reproductive hormones, and many other factors influence fat formation (Fried, et al., *Diverse Roles of Adipose Tissue in the Regulation of Systemic Metabolism and Energy Balance*, In: Bray, G. A., Bouchard, C., James, W. P., eds. Handbook of Obesity, New York, Marcel Dekker, pp 397–414, 1977). The fat accumulation control system involves many different cellular processes, including energy expenditure, digestion, absorption, transport, and storage of nutrient fuels. Thus, it is extremely difficult to treat obesity by correcting a single biochemical pathway due to the contributions of multiple physiochemical abnormalities.

Drug treatment for obesity has been disappointing since almost all drug treatments for obesity were associated with undesirable side effects that contributed to their termination. Available pharmacotherapies have included Sibutramine, Orlistat, fenfluramine and dexfenfluramine. Fenfluramine and dexfenfluramine were withdrawn from the market in 1997 because of associated cardiac valvulopathy (Connolly, et al., *Valvular Heart Disease Associated With Fenfluramine-Phentermine*, New Engl J Med 337–581–588, 1997). Therefore, health care professionals continue to be reluctant to use pharmacotherapy in the management of obesity. Complimentary approaches to pharmacotherapy will therefore be of great interest to the public.

The better choice for treatment of obesity is to reduce food intake. A number of monoamines and neuropeptides are known to reduce food intake (Bray, et al., *Pharmacological Treatment of Obesity*, Am J Clin Nutr 55:151S–319S, 1992). Although body weight loss is effective, these sympathomimetic drugs cause side effects including pulmonary hypertension, neuroanatomic changes, and a typical valvular heart diseases. Thus, nutrition and dietary restriction are most desirable for weight loss. However, long-term success of dietary regulation is low because of noncompliance. The loss of motivation to change dietary habits necessary to consume less fat and fewer calories results in regaining weight.

Previous studies have indicated that prostaglandins (PGs) and arachidonic acid (AA), a precursor of prostaglandins, chelate zinc and regulate intestinal zinc absorption and secretion (Song et al., *Am. J. Physiol.* 234:E99 (1979); Song et al., *J. Nutr.* 109:2151 (1979); Koletzko et al., *Eur. J. Pediatr.* 143:310 (1985); Song et al., *Prost. Leuko. Med.*

17:159 (1984)). Isolated intestinal segments from diabetic rats showed significantly decreased intestinal zinc absorption capacity in Ussing chamber experiments (Song et al., *Life Sci.* 42:687 (1988)). When AA was added to the segment-bathing medium, zinc uptake increased significantly compared to controls. Although oral administration of low doses of AA decreased the intestinal zinc absorption rate, high doses of AA increased zinc absorption in non-diabetic rats (Song et al., *Prost. Leuko. Med.* 17:159 (1984)).

It has been reported that PGs and AA play important roles in the regulation of insulin release (Aalusha et al., "Prostaglandins and diabetes mellitus" in *Diabetes Mellitus, Theory and Practice*, ed. Ellenberg et al., pp. 295–308), and participate in numerous diabetes-related metabolic activities (Robertson, *Med. Clin.* 65:759 (1984); Katayama et al., *Hypertension* 7:554 (1985); Harrison et al., *Diabetologia* 18:65 (1980); Subbiah et al., *Biochem. Med.* 23:231 (1995); Johnson et al., *Lancet* 1:325 (1979); Shakir et al., *J. Clin. Invest.* 60:747 (1977); Goto et al., *Diabetes* 41:1644 (1992)).

Despite this background understanding, there still has not emerged an effective means of alleviating the symptoms associated with obesity by purposefully manipulating zinc metabolism in obese animals. New compositions and methods that fill this need are disclosed herein.

SUMMARY OF THE INVENTION

One aspect of the present invention relates to a method of treating an overweight mammal to alleviate symptoms associated with being overweight. In another embodiment of the invented method, the mammal is obese. This method includes the step of administering at least once daily to the overweight or obese mammal a pharmaceutical composition that includes zinc and cyclo-Hispro (CHP) in an amount sufficient to reduce body weight and food intake. The pharmaceutical composition administered to the mammal includes a zinc cation and an anion, where the amount of zinc cation can range from about 1 to about 100 mg, preferably about 5 to about 50 mg, and more preferably about 10 to about 25 mg. For an average human weighing 70 kilograms this is equivalent to the amount of zinc cation ranging from about 0.01 to about 1.4 mg/kg/day, preferably about 0.07 to about 0.7 mg/kg/day, and more preferably about 0.1 to about 0.4 mg/kg/day. In one embodiment, the amount of cyclo-Hispro present in the administered pharmaceutical composition can range from about 0.5 to about 50 mg, with a more preferred range extending from about 5 to about 30 mg. For an average human weighing 70 kilograms this is equivalent to the amount of cyclo-Hispro ranging from about 0.007 to about 0.7 mg/kg/day, more preferably from about 0.07 to about 0.4 mg/kg/day. In another embodiment, the amount of cyclo-Hispro present in the administered pharmaceutical composition can range from about 0.5 to about 100 mg, with a more preferred range extending from about 10 to about 70 mg. For an average human weighing 70 kilograms this is equivalent to the amount of cyclo-Hispro ranging from about 0.007 to about 1.4 mg/kg/day, more preferably from about 0.1 to about 1 mg/kg/day. The cyclo-Hispro may be present in the form of a soybean protein hydrolysate enriched for cyclo-Hispro. In a preferred embodiment, the pharmaceutical composition further comprises from about 0.1 to about 10 mg of L-histidine, or 0.001 to about 0.1 mg/kg/day. In a preferred embodiment of the invented method, the pharmaceutical composition is administered orally, and may be administered two to four times daily. By treating obesity, the pharmaceutical compositions described herein also treat hypertension and high cholesterol.

A second aspect of the invention relates to another method of treating an overweight or obese mammal to alleviate symptoms associated with obesity. This method includes the steps of administering at least once daily to the obese mammal a pharmaceutical composition that includes zinc and arachidonic acid in an amount sufficient to reduce body weight and food intake. The pharmaceutical composition administered to the mammal includes a zinc cation and an anion, where the amount of zinc cation can range from about 1 to about 100 mg, more preferably 5 to about 50 mg or from about 0.01 to about 1.4 mg/kg/day, preferably about 0.07 to about 0.7 mg/kg/day for a 70 kg human. The amount of arachidonic acid present in the administered pharmaceutical composition can range from about 1 mg to about 1000 mg, with a preferred range of about 10 mg to about 700 mg, preferably from about 25 mg to about 400 mg. More preferably from about 50 mg to 300 mg, with a preferred dosage of about 120 mg. For an average human weighing 70 kg, the equivalent amount of arachidonic acid ranges from about 0.01 to about 14 mg/kg/day, with a preferred range of about 0.14 to about 10 mg/kg/day, preferably from about 0.3 to about 6 mg/kg/day. More preferably from about 0.7 to about 4.3 mg/kg/day, with a preferred dosage of about 1.7 mg/kg/day. In a preferred embodiment, the pharmaceutical composition further comprises from about 0.1 to about 10 mg of L-histidine, or 0.001 to about 0.1 mg/kg/day. In a preferred embodiment of the invented method, the pharmaceutical composition is administered orally, and may be administered two to four times daily. By treating obesity, the pharmaceutical compositions described herein also treat hypertension and high cholesterol.

A third aspect of the invention relates to another method of treating an overweight or obese mammal to alleviate symptoms associated with obesity. This method includes the steps of administering at least once daily to the obese mammal a pharmaceutical composition that includes L-histidine in an amount sufficient to reduce food intake and body weight. In a preferred embodiment, the L-histidine is present in the administered pharmaceutical composition in an amount ranging from about 0.1 to about 25 mg (about 0.001 to about 0.4 mg/kg/day). In another preferred embodiment of the invented method, the administered pharmaceutical composition further includes a zinc cation and an anion. When the administered composition includes a zinc cation and an anion, the zinc cation is present in an amount ranging from about 5 to about 50 mg. According to another preferred embodiment of the invented method, the administered composition includes L-histidine and cyclo-Hispro. In yet another preferred embodiment of the invented method, the pharmaceutical composition which is administered includes L-histidine and arachidonic acid. When arachidonic acid is included in the composition, the arachidonic acid is present in an amount from about 1 mg to about 500 mg, with a preferred range of about 25 mg to about 400 mg. More preferably from about 50 mg to 300 mg, with a preferred dosage of about 120 mg. Compositions containing arachidonic acid additionally may include a zinc cation, which may be present in an amount ranging from about 5 to about 50 mg. For embodiments of the invented method in which the administered composition includes a zinc cation, the L-histidine included in the pharmaceutical composition is present in an amount ranging from about 0.1 mg to about 1.0 mg. When cyclo-Hispro is included in the administered composition, the cyclo-Hispro is present in an amount ranging from about 5 mg to about 30 mg. In a highly preferred embodiment of the invented method, the administered composition includes L-histidine, arachidonic acid and a zinc salt. In this highly preferred embodiment the zinc cation of the zinc salt is present in an amount ranging from about 5 mg to about 50 mg, the arachidonic acid included in the pharmaceutical composition is present in an amount ranging from about 1 mg to about 500 mg, and the L-histidine included in said pharmaceutical composition is present in an amount ranging from about 0.1 mg to about 1.0 mg. Finally, the pharmaceutical composition can be administered orally, and can be administered two to four times daily. By treating obesity, the pharmaceutical compositions described herein also treat hypertension and high cholesterol.

A fourth aspect of the invention relates to relates to a soybean protein hydrolysate (SPH) enriched for cyclo-Hispro which can be used as part of a method of treating an overweight or obese mammal to alleviate symptoms associated with obesity. The SPH is obtained by a process wherein a soybean protein is hydrolyzed to produce a soybean protein hydrolysate. In one embodiment, the SPH is prepared by acid hydrolysis of the soybean protein. In another embodiment, the SPH is prepared by alkaline hydrolysis of the soybean protein. The SPH is then refluxed in the presence of an alcohol/carbonate mixture. Preferably the alcohol in the alcohol/carbonate mixture is EtOH. The preferred carbonate in the alcohol/carbonate mixture is $KHCO_3$. Additionally the CHP content of the SPH may be determined by radio immune assay (RIA) and/or HPLC-MS analysis. In another embodiment, the SPH also includes zinc. In further embodiments, the SPH can be administered as a component of a functional food or food supplement.

The compositions of the present invention can be formulated into foods or food supplements. These include, but are not limited to, powders for addition to food, protein shakes, meal replacement or energy bars, snack foods and the like. These embodiments can also include zinc and/or arachidonic acid. Alternatively, the compositions can be formulated into nutritional supplements, taking forms such as capsules, tablets, gelcaps and the like. The compositions can be formulated neat, or can be accompanied by fillers, excipients and other additional ingredients well known within the pharmaceutical, nutriceutical and functional food industries.

BRIEF DESCRIPTION OF THE DRAWINGS

FIG. 1 is an illustration of the effect of cyclo-Hispro feeding on the body weight changes in G-K rats.

FIG. 2 is an illustration of the effect of cyclo-Hispro feeding on the body weight gains in young G-K rats. These embodiments can also include Zinc and/or cyclo-Hispro.

FIG. 3 illustrates the effects of cyclo-Hispro feeding on the body weight gains in C57BL6J mice. These foods or food supplements include, but are not limited to protein shakes, meal replacement or energy bars, snack foods and the like.

FIG. 4 illustrates the effects of zinc plus cyclo-Hispro on the body weight changes in aged overweight S-D rats.

FIG. 5 illustrates the effects of zinc plus cyclo-Hispro on the body weight changes in aged normal weight S-D rats.

FIG. 6 illustrates the effects of zinc or zinc plus cyclo-Hispro feeding on the food intake in G-K rats.

FIG. 7 illustrates the effects of zinc or zinc plus cyclo-Hispro on the sucrose solution intake in C57BL/6J mice.

FIG. 8 illustrates the effects of zinc or zinc plus cyclo-Hispro feeding on water intake in G-K rats.

FIG. 9 illustrates the effects of zinc or zinc plus cyclo-Hispro feeding on water intake in S-D rats.

FIG. 10 illustrates the effects of zinc or zinc plus various doses of AA feeding on water intake in G-K rats.

FIG. 11 illustrates the effects of zinc or zinc plus cyclo-Hispro feeding on body weight changes in 1.5 month old male G-K rats compared to DW treated rats.

FIG. 12 illustrates the effects of cyclo-Hispro on the body weight gains in male G-K rats after cessation of treatment.

FIG. 13 illustrates the effects of cyclo-Hispro on the body weight gains in female G-K rats after cessation of treatment.

DETAILED DESCRIPTION OF THE PREFERRED EMBODIMENT

I have discovered that pharmaceutical compositions comprising zinc plus cyclo-Hispro or arachidonic acid are useful for treating obesity in mammals. My earlier work, disclosed in U.S. Pat. No. 5,834,032, the disclosure of which is herein incorporated by reference in its entirety, provided pharmaceutical compositions comprising zinc and either cyclo-Hispro (CHP) or arachidonic acid (AA) for treating diabetes in mammals. Herein, I disclose a method for treating obesity. I also disclose a process to purify and manufacture cyclo-Hispro.

Certain aspects of the present invention relate to the use of pharmaceutical compositions. In a preferred embodiment, pharmaceutical compositions used in connection with the present invention comprise: (1) a zinc salt, (2) cyclo-Hispro and/or (3) arachidonic acid, and (4) at least one pharmaceutically acceptable excipient. The most preferred embodiment of these ingredients includes zinc and CHP or zinc and arachidonic acid. In this invention, these ingredients of the pharmaceutical compositions can be included in "purified" form. By the use of the term "purified", it is intended to mean that these ingredients are in a form enriched relative to the form in which they can be obtained from nature, such as in a prostate extract. The purified ingredients can be obtained either by enriching from a natural source thereof, or by a chemically synthetic method. Thus, the use of the term "purified" does not necessarily imply that these ingredients are completely free, or even substantially free, of other components. Nevertheless, a "purified" ingredient is enriched relative to its concentration in a natural prostate extract.

The pharmaceutical compositions prepared according to the present invention preferably can be packaged in tablet or capsule form by procedures that are well known in the pharmaceutical arts. As referred to herein, numerical values for zinc represent masses or concentrations of the zinc component of a zinc salt. Examples of zinc salts useful in connection with the invention include zinc chloride and zinc sulfate. In one embodiment, the amount of zinc cation can range from about 1 to about 100 mg, preferably about 5 to about 50 mg, and more preferably about 10 to about 25 mg. In one embodiment, the amount of cyclo-Hispro present in the administered pharmaceutical composition can range from about 0.5 to about 50 mg, with a more preferred range extending from about 5 to about 30 mg. In another embodiment, the amount of cyclo-Hispro present in the administered pharmaceutical composition can range from about 0.5 to about 100 mg, with a more preferred range extending from about 10 to about 70 mg. The amount of arachidonic acid present in the administered pharmaceutical composition can range from about 1 mg to about 1000 mg, with a preferred range of about 10 mg to about 700 mg, preferably from about 25 mg to about 400 mg. More preferably from about 50 mg to 300 mg, with a preferred dosage of about 120 mg.

In one embodiment for treatment of human beings, each tablet or capsule preferably contains about 1 to about 100 mg of zinc, preferably about 5 to about 50 mg zinc, and about 0.5 to about 100 mg of cyclo-Hispro, in addition to the pharmaceutically acceptable excipient or excipients. In another embodiment, each tablet or capsule preferably contains about 1 to about 100 mg of zinc, preferably about 5 to about 50 mg zinc, and about 1 mg to about 1000 mg of arachidonic acid, in addition to the pharmaceutically acceptable excipient or excipients. Thus, a preferred weight ratio of zinc cation to cyclo-Hispro is from about 1:100 to about 100:0.5. When the composition includes arachidonic acid, a preferred weight ratio of zinc cation to arachidonic acid is from about 1:1000 to about 100:1. It is believed that compositions with these ratios of ingredients are effective in treating a wide range of mammals.

In one embodiment, zinc cation with arachidonic acid is effective to treat obesity. In these embodiments, zinc can range from about 1 to about 100 mg, preferably about 5 to about 50 mg, and more preferably about 10 to about 25 mg. For an average human weighing 70 kilograms this is equivalent to the amount of zinc cation ranging from about 0.01 to about 1.4 mg/kg/day, preferably about 0.07 to about 0.7 mg/kg/day, and more preferably about 0.1 to about 0.4 mg/kg/day. In one embodiment, the amount of cyclo-Hispro present in the administered pharmaceutical composition can range from about 0.5 to about 50 mg, with a more preferred range extending from about 5 to about 30 mg. For an average human weighing 70 kilograms this is equivalent to the amount of cyclo-Hispro ranging from about 0.007 to about 0.7 mg/kg/day, more preferably from about 0.07 to about 0.4 mg/kg/day. In another embodiment, the amount of cyclo-Hispro present in the administered pharmaceutical composition can range from about 0.5 to about 100 mg, with a more preferred range extending from about 10 to about 70 mg. For an average human weighing 70 kilograms this is equivalent to the amount of cyclo-Hispro ranging from about 0.007 to about 1.4 mg/kg/day, more preferably from about 0.1 to about 1 mg/kg/day. Pharmaceutically acceptable carriers, diluents or excipients are also included.

In another embodiment the pharmaceutical composition comprises zinc and arachidonic acid where the amount of zinc ranges from about 1 to about 100 mg, more preferably 5 to about 50 mg or from about 0.01 to about 1.4 mg/kg/day, preferably about 0.07 to about 0.7 mg/kg/day for a 70 kg human. The amount of arachidonic acid present in the administered pharmaceutical composition can range from about 1 mg to about 1000 mg, with a preferred range of about 10 mg to about 700 mg, preferably from about 25 mg to about 400 mg. More preferably from about 50 mg to 300 mg, with a preferred dosage of about 120 mg. For an average human weighing 70 kg, the equivalent amount of arachidonic acid ranges from about 0.01 to about 14 mg/kg/day, with a preferred range of about 0.14 to about 10 mg/kg/day; preferably from about 0.3 to about 6 mg/kg/day. More preferably from about 0.7 to about 4.3 mg/kg/day, with a preferred dosage of about 1.7 mg/kg/day. Pharmaceutically acceptable carriers, diluents or excipients are also included.

Another composition useful in connection with the invention can also be formulated into a tablet or capsule. In one embodiment for treatment of human beings, tablets or capsules prepared with this composition each will preferably contain about 1 to about 100 mg zinc, preferably about 5 to about 50 mg of zinc, about 0.1 to about 25 mg of L-histidine, preferably about 0.1 to about 10 mg L-histidine, and a pharmaceutically acceptable excipient or excipients. This composition can optionally include cyclo-Hispro in an amount ranging from about 0.5 mg to about 100 mg, about 0.5 mg to about 50 mg, more preferably from about 10 mg to about 30 mg. Another optional ingredient in the second composition would be about 1 mg to about 1000 mg of arachidonic acid. Thus, a preferred weight ratio of zinc cation to L-histidine is from about 100:0.1 to about 1:25. When this composition includes cyclo-Hispro, a preferred weight ratio of zinc cation to cyclo-Hispro is from about 100:0.5 to about 1:100, and when the composition includes arachidonic acid, a preferred weight ratio of zinc cation to arachidonic acid is from about 100:1 to about 1:1000. It is believed that compositions with these ratios of ingredients are effective in treating a wide range of mammals.

Suitable excipients for tablets and capsules include inert diluents, such as safflower oil, lecithin, inositol, soybean shortening oil, gelatin, acacia, glycerin, titanium oxide and soybean oil. The coating of the capsules can be gelatin or a soluble polymer, as is well understood in the art. The tablets or capsules are suitable for oral administration according to a daily administration regimen.

The pharmaceutical compositions described herein are useful for the treatment of obesity. In particular, obesity can be treated by administering the composition of the present invention to an obese mammal in a quantity sufficient to reduce body weight and food intake. By treating obesity, the pharmaceutical compositions described herein are also treating hypertension and high cholesterol. In one embodiment, doses for obese or overweight patients stated as the quantity of zinc, are from about 20 mg to about 80 mg of zinc per day. These doses can be adjusted by one of ordinary skill in the art according to such factors as the weight, age, sex, and state of health of the patient, as well as according to the response to a particular dosage.

The experimental results disclosed herein now identify several defined chemical species which can be combined to result in a composition that is substantially as effective at controlling body weight and food intake. Accordingly, I have created a new composition useful for treating obesity.

I have determined that recreational physical therapy together with well-controlled food intake and dietary supplements such as zinc plus AA (ZA) or zinc plus CHP (ZC) are the most desirable treatments for body weight control. I established that treatment of obese and overweight patients with ZA and/or ZC is safe and effective in controlling body weight. As disclosed below, I have identified various chemical combinations of zinc, L-histidine, arachidonic acid and/or cyclo-Hispro that can be used for controlling obesity in mammals.

Although other materials and methods similar or equivalent to those described herein can be used in the practice or testing of the present invention, the preferred methods and materials are now described.

I believe that Zinc both reduces appetite and improves energy expenditure (Mantozoros, et al. *Zinc May Regulate Serum Leptin Concentrations in Humans*, J Am Coll Nutr 17:270–275, 1998). AA and cyclo-Hispro play a role in the regulation of zinc metabolism (Song, et al., *The Role of Prostaglandin E2 in Zinc Absorption in the Rat*, Am J Physiol 234:E99–E105, 1978; Song, et al., *Effect of Oral Administration of Arachidonic Acid on Prostaglandin and Zinc Metabolism in Plasma and Small Intestine of the Rat*, Pros Leuko Med 17:159–166, 1984; Rosenthal, et al., *Effects of Arachidonic Acid and Cyclo (his-pro) on Zinc Transport Across Small Intestine and Muscle Tissues*, Life Sci.

70:337–348, 2001), and cyclo-Hispro enhances reduction of food intake induced by amphetamine (Kow, et al., *Cyclo (his-pro) Potentiates the Reduction of Food Intake Induced by Amphetamine, Fenfluramine, or Serotonin*, Pharamcol Biochem Behav 38:365–369, 1991). In my recent studies, dietary feeding of ZC for one month, significantly decreased body weight in 10 month old genetically diabetic Wistar G-K rats (FIG. 1), without affecting growth rates of young rats (FIG. 2). Body weight gain was also reduced in 8 month old 32% sucrose fed C57BL.6J mice (FIG. 3). Dietary feeding of ZC also decreased body weight and water and food intake in ob/ob mice (Table 1). ZC feeding 12–18 months old overweight S-D rats also significantly decreased body weights of these rats (FIG. 4) without affecting normal (body) weight 8 month old normal Sprague Dawley rats (FIG. 5). Details of these experiments are provided herein below under the heading "Experimental Data."

Human obesity is characterized by leptin resistance (Caro, et al., *Decreased Cerebrospinal Fluid/Serum Leptin Ratio in Obesity: A Possible Mechanisms for Leptin Resistance*, Lancet 348:159–161, 1996; Van Heek, et al., *Diet-Induced Obese Mice Develop Peripheral, but not Central, Resistance to Leptin*, J Clin Invest 99:385–390, 1997). Leptin resistance may develop in humans during the aging process. However, the leptin receptor initiated signal transduction mechanisms are largely unknown, and no agent for treatment of human obesity is satisfactory, no agent for the treatment or prevention of leptin resistance is currently available. Thus, new agents that are effective with little or no overt side effects are highly desirable, and without wishing to be bound by any theory, I believe that ZC and/or ZA reduces body weight by ameliorating leptin-resistance.

Background Studies Leading Toward Developing a Novel Anti-obese Agent:

Since zinc is involved in gene expression, cell growth, and cell division (Faclchuk, et al., *Role of Zinc in Cell Division of Euglena Gracilis*, J Cell Sci 17:57–78, 1975), I began to examine intestinal zinc absorption mechanisms. I was the first to demonstrate that prostaglandins (PGs) regulated intestinal zinc absorption (Song, et al., *The Role of Prostaglandin E2 in Zinc Absorption in the Rat*, Am J Physiol 234:E99–E105, 1978). Subsequently, I demonstrated that AA (Song, et al., *Effect of Oral Administration of Arachidonic Acid on Prostaglandin and Zinc Metabolism in Plasma and Small Intestine of the Rat*, Pros Leuko Med 17:159–166, 1984), steroid hormones (Song, et al., *Prostaglandin Interacts with Steroid Sex Hormones in the Regulation of Intestinal Zinc Transport*, Comp Biochem Physiol 101A:477–481, 1992), L-histidine (Pham, et al., *Factors Affecting Zinc Flux Rates of Rat Intestinal Segments Mounted into Ussing Chambers*, Biochem Arch 7:213–219, 1991), and CHP (Rosenthal, et al. *Effects of Arachidonic Acid and Cyclo (his-pro) on Zinc Transport Across Small Intestine and Muscle Tissue*, Life Sci 70:337–348, 2001) influence intestinal zinc absorption and muscle tissue zinc uptake. Others reported that citric acid chelates zinc and stimulates intestinal zinc absorption (Hurley, et al., *Zinc Citrate, Human Milk, and Acrodermatitis Enteropathica*, The Lancet I:677, 1979). Although a vast number of papers on zinc metabolism are published annually, intestinal zinc absorption mechanisms are not yet clearly established. PGs were initially isolated from prostate (Von Euler, U.S., *Zur Kenntnis der Pharmakologischen Wirkungen von Nativsekreten und Extrakten Mannlicher Accessorischer Geschlechtsdreisen*, Arch Exp Path Pharamak 175:78–84, 1934), and relatively high amounts of zinc (Halstead, et al., *A conspectus of Research of Zinc Requirements of Man*, J. Nutr 104:345–349, 1974), citric acid (Arver, S., *Zinc and Zinc Ligands in Human Seminal Plasma III. The Principal Low Molecular Weight Zinc Ligand in Prostatic Secretio nand Seminal Plasma*, Acta Physiol Scand 116:67–73, 1982), testosterone (Belanger, et al., *Comparison of Residual C-19 Steriod in Plasma, and Prostatic Tissues of Human, Rat and Guinea Pig After Castration: Unique Importance of Extratesticular Androgens in Men*, J Steroid Biochem 32:695–698, 1989), and CHP (Pekary et al., *High Concentrations of p-Glu-His-Pro-NH$_2$ (Thyrotrophin-Releasing Hormone) Occur in Rat Prostate*, Peptides 4:915–919, 1983) were also found in the prostate. Characteristically, diabetic patients have low testosterone levels (Fushimi, et al., *Low Testosterone Levels in Diabetic Men and Animals: A Possible Role in Testicular Impotence*, Diabet Res Clin Pract 6:297–301, 1989). Thus, I believe that all of these constituents may synergistically affect cellular zinc metabolism, and these constituents in the prostate may stimulate intestinal zinc absorption. As I expected, prostate extract (PE) strongly stimulated intestinal zinc absorption (Song, et al., *Effects of Animal Prostate Extract on Zinc Metabolism in Diabetic Rats*, Diabet Res 31:157–170, 1996).

Since it is known that diabetic animals and humans are afflicted with impaired intestinal zinc absorption and low plasma zinc levels, I examined the effects of PE on clinical signs of streptozotocin-treated diabetic rats. (Song, et al., *Intestinal zinc transport: Influence of streptozotocin-induced diabetes, insulin and arachidonic acid*. Life Sci 42:687–694, 1988; Kinlaw, et al., *Abnormal zinc metabolism in Type II diabetes mellitus*. Am J Med 75:273–77, 1983; Gochishan, et al., *Intestinal transport of zinc in the diabetic rat*. Life Sci 32:1735–41, 1983; Johnson, et al., *Intestinal absorption and excretion of zinc in streptozotocin-diabetic rats as affected by dietary zinc and protein*. J Nutr 115: 1217–27, 1985; Killrich, et al., $^{65}$*Zn absorption in patients with insulin-dependent diabetes mellitus assessed by whole-body counting technique*. Clin. Chim. Acta 189:13–18, 1990; Levine, et al., *Tissue zinc status of genetically diabetic and streptozotocin-induced diabetic mice*. Am J Clin Nutr 37:382–386, 1983; Chooi, et al., *Influence of age and sex on plasma zinc levels in normal and diabetic individuals*. Nutr Metab 20:135–142, 1976; Song, et al., *Effects of animal prostate extract on zinc metabolism in diabetic rats*. Diabet Res 31:157–170, 1996). Dietary feeding of PE plus zinc lowered both blood glucose levels and intake of water and food in streptozotocin-induced diabetic rats. Thus, I made softgel capsules containing 200 mg of prostate powder plus 20 mg zinc and treated Type 2 diabetic patients with these gel-capsules four times a day for three months. Those patients who took 2–4 gel capsules/day for three months exhibited significantly improved oral glucose tolerance test (OGTT) without increasing plasma insulin levels, and decreased blood HbA$_{1c}$ and urine glucose levels (Song, et al., *Effects of animal prostate extract on zinc metabolism in diabetic rats*. Diabet Res 31:157–170, 1996). These results suggest that PE ameliorates insulin resistance. Although I have not determined obesity-related parameters in these patients, I believe that those who showed improved OGTT and HbA1c levels also experienced decreased intake of water and food and/or improved processing of sugars resulting in less deposition of fat. I believe that some constituents in the prostate such as zinc, CHP and AA work synergistically to control intake of food and water, thus affecting body weight control.

Importance of Zinc in the Control of Obesity:

Zinc activates the insulin receptor β-subunit (Ezaki O: *IIb group metal ions ($Zn^{2+}$, $Cd^{2+}$, $Hg^{2+}$) stimulate glucose transport activity by post-insulin receptor kinase mechanism in rat adipocytes*. J Biol Chem 264:16118–16122, 1989; Tang, et al., *Zinc has an insulin-like effect on glucose transport mediated by phosphoinositol-3-kinase and AKT in 3 T#-L1 fibroblasts and adipocytes*. J Nutr 131:1414–1420, 2001). Zinc deficiency results in hypoleptinemia in animals and humans and supplementation with zinc increases leptin synthesis in humans (Mangian, et al., *Zinc deficiency suppresses plasma leptin concentration in rats*. J Nutr. Biochem. 9:47–51. 1998; Mantzoro, et al., *Zinc may regulate serum leptin concentrations in humans*. J Am Coll Nutr 17:270–275, 1998; Chen, et al., *Zinc may be mediator of leptin production in humans*. Life Sci 66:2143–2149, 2000). Zinc, in turn, ameliorates sucrose-induced obesity in mice and in rats (Chen, et al., *Zinc-induced hyperleptinemia relates to the amelioration of sucrose-induced obesity with zinc repletion*. Obes Res 8:525–529, 2000; Bock, et al. *Mineral content of the diet alters sucrose induced obesity in rats*. Physiol Behav 57:659–668, 1995). Thus, I have concluded that zinc plays an important role in the synthesis of leptin. However, plasma zinc levels in obese animals and humans are lower than those in non-obese counterparts (Di Martino, et al., *Relationship between zinc and obesity*. J Med 24:177–183, 1993). Hypothalamic neuropeptide Y (NPY) levels are increased in zinc-deficient rats (Lee, et al., *Zinc deficiency increases hypothalamic neuropeptide Y and neuropeptide Y mRNA levels and does not block neuropeptide Y-induced feeding in rats*. J Nutr 128:1218–1223, 1998). This further supports my conclusion that adequate zinc nutriture is needed to control appetite, and hence to control obesity. However, excess zinc supplementation may aggravate obesity by increasing gene expression and adipocyte growth (Taneja, et al., *Excess bioavailability of zinc may cause obesity in humans*. Experientia 52:31–33, 1996). Zinc also effectively increases lipogenesis in adipocytes (Chen, et al., *Effects of zinc supplementation on the plasma glucose level and insulin activity in genetically obese (ob/ob) mice*. Biol Trace Elem Res 61:303–311, 1998). Therefore, I believe that balanced zinc nutriture is very important in the control of body weight in both animals and humans.

Without wishing to be bound by any theory, I believe that leptin resistance is highly likely to be one of the major causes of obesity in humans, characterized with impaired leptin signal transduction (Scarpace, et al., *Hypothalamic leptin resistance is associated with impaired leptin signal transduction in aged obese rats*. Neuroscience 104:1111–1117, 2001). Therefore it is very important to understand the role of zinc in the leptin-receptor mediated signal transduction mechanism. Similar to the stimulation of insulin-receptor phosphorylation by zinc, I believe that zinc can stimulate phosphorylation of leptin-receptor (LR) to activate signal transducer and activator of transcription (STAT3) to inhibit NPY synthesis in brain cells. (Ezaki O: *IIb group metal ions ($Zn^{2+}$, $Cd^{2+}$, $Hg^{2+}$) stimulate glucose transport activity by post-insulin receptor kinase mechanism in rat adipocytes*. J Biol Chem 264:16118–16122, 1989; Tang, et al, *Zinc has an insulin-like effect on glucose transport mediated by phosphoinositol-3-kinase and AKT in 3 T#-L1 fibroblasts and adipocytes*. J Nutr 131:1414–1420, 2001)

Adequate Arachidonic Acid (AA) Plays a Role in the Control of Obesity:

Below normal levels of AA have been reported in serum of obese humans and in organ tissues from obese Zucker rats. (Phinney, et al., *Obesity and weight loss alter polyunsaturated lipid metabolism in humans*. Am J Clin Nutr 51:831–838, 1991; Guesnet, et al., *Tissue phospholipid fatty acid composition in genetically lean and obese Zucker female rats on the same diet*. Lipids 25:517–522, 1990; Wahle, et al., *Regulation of polyunsaturated fatty acid metabolism in tissue phsopholipids of obese (fa/fa) and lean (Fa/-) Zucker rats. I Effect of dietary lipids on cardiac tissues*. Lipids 26:16–22, 1991). Phinney et al. suggested that abnormal AA metabolism contributes to the etiology of Zucker obesity, and supplementation of AA improved the obesity syndrome (Phinney, et al., *Abnormal polyunsaturated lipid metabolism in the obese Zucker rat, with partial metabolic correction by γ-linolenic acid administration*. Metabolism 42:1127–1140, 1993; Loftus, et al, *Reduced food intake and body weight in mice treated with fatty acid synthase inhibitors*. Science 288:2379–2381, 2000). Fat cell differentiation is a critical aspect of obesity, since fatty acid synthesis is directly related to the control of appetite and body weight. AA is the precursor of 2 series of prostaglandins. $PGF_{2\alpha}$ induces anorexia and blocks adipogenesis through activation of peroxisome proliferator-activated receptor gamma (PPAR gamma) and mitogen-activated protein kinase, while $PGJ_2$ activates adipogenesis (Doggett, et al. *Anorectic activity of prostaglandin precursors*. Brit J Pharmacol 60:417–423, 1977; Reginanato, et al., *Prostaglandins promote and block adipogenesis through opposing effects on peroxisome proliferator-activated receptor gamma*. J Biol Chem 273:1855–1858, 1998). Thus, I believe that the balance between $PGF_{2\alpha}$ and $PGJ_2$ signaling may be one of the key functions for the control of body weight. AA levels in serum, liver and kidney are lower in genetically obese Zucker rats than in normal rats due to the decrease of delta 5-desaturase-activity (Guesnet, et al. *Tissue phospholipid fatty acid composition in genetically lean and obese Zucker female rats on the same diet*. Lipids 25:517–522, 1990). These findings support my conclusion that adequate AA and PG metabolism is also crucial in the control of obesity.

Implication of Cyclo-Hispro (CHP) as an Obesity Treating Agent:

CHP, a cyclic form of L-histidine and proline, stimulates intestinal zinc transport and cellular zinc uptake (Rosenthal, et al., *Effects of arachidonic acid and cyclo (his-pro) on zinc transport across small intestine and muscle tissues*. Life Sci. 70:337–348, 2001). Plasma histidine-proline-rich glycoprotein contains unusual tandems of histidine-proline, and is relatively abundant in plasma. This glycoprotein plays a role in the cellular zinc transport process (Borza, et al., *Histidine-proline-rich glycoprotein as plasma pH sensor*. J Biol Chem 273:5493–5499, 1998). Although CHP is a metabolite of thyrotropin releasing hormone (TRH), CHP can be synthesized from different biochemical sources, including histidine-proline-rich glycoprotein (Morgan W T. *Human serum histidine-proline-rich glycoprotein*. Biochim Biophys Acta 533:319–333, 1978). High levels of CHP are present in many food sources, and are readily absorbed in the gut without chemical or enzymatic destruction ((Hilton, et al., *Food contains the bioactive peptide, cyclo (his-pro)*. J Clin Endocrinol Metab 75:375–378, 1992; Mizuma, et al., *The bioactive peptide cylco (his-pro) may be absorbed following ingestion of nutritional supplements that contain it*. J Am coll Nutr 15:175–179, 1996). CHP intake decreases food intake in rats and humans (Morley, et al., *Histidyl-proline diketopiperazine decreases food intake in rats*. Brain Res. 210:475–478, 1981; Steiner, et al., *Histidyl proline diketopiperazine (cyclo [his-pro]) in eating disorders*. Neuropeptides 14:185–189, 1989). It specifically decreases fat intake and some degree of carbohydrate intake. Interestingly, CHP levels in the brains of obese rats are elevated compared to lean normal rats (Prasad, et al., *A paradoxical elevation of brain cyclo (his-pro) levels in hyperphargic obese Zucker rats*. Brain Res 699:149–153, 1995). Thus, I have concluded that there is a clear relationship between CHP metabolism and obesity syndrome. Although the mechanisms are not clearly understood, I have concluded that CHP is involved in the control of satiety in the brain. (Morley, et al. *Histidyl-proline diketopiperazine decreases food intake in rats*. Brain Res. 210:475–478, 1981. Steiner, et al., *Histidyl proline diketopiperazine (cyclo [his-pro]) in eating disorders*. Neuropeptides 14:185–189, 1989.) I further believe that CHP reduces food intake by interacting with serotonin and fenfluramine, which are known anti-obesity drugs. (Kow, et al., *Cyclo (his-pro) potentiates the reduction of food intake induced by amphetamine, fenfluramine, or serotonin*. Pharamcol Biochem Behav 38:365–369,1991.) CHP is distributed all over the human body and present in most protein-containing foods. (Prasad, et al., *A paradoxical elevation of brain cyclo (his-pro) levels in hyperphargic obese Zucker rats*. Brain Res 699:149–153, 1995; Hilton, et al., *Food contains the bioactivepeptide, cyclo (his-pro)*. J Clin Endocrinol Metab 75:375–378, 1992.) Furthermore, intraventricular administration of CHP significantly reduces water intake. (Ishihara, et al., *Intraventricular administration of cyclo (his-pro), metabolite of thryrotrophin-releasing hormone (TRH), decreases water intake in the rat*. Proc Soc Exp Biol Med 178:623–628, 1985.) It has been observed that obesity and increased water intake are linked in certain pathological conditions (66,67). Thus, I believe that supplementation of supraphysiological doses of CHP may be very effective in the control of body weight by decreasing food and water intake. However, there has not yet been a systematic study confirming that CHP reduces or prevents obesity. One aspect of my invention is that zinc plus CHP is effective in the control of body weight.

Since PG and zinc metabolism are closely related to the pathophysiology of diabetes and obesity (36–56), I investigated intestinal zinc absorption mechanisms in diabetic rats and the effect of the PG precursor, AA, on the intestinal zinc transport rate of diabetic rats (32). Although AA increased the zinc uptake rate of jejunal segments of diabetic rats, it did not enhance the zinc transport rate into the circulatory system. These findings support my conclusion that AA not only serves as zinc chelating agent, but more importantly it is the PG precursor, which regulates intracellular zinc absorption.

My previous studies with normal rats indicated that intestinal zinc absorption increased when AA doses were above 1.0 mg/200 g body weight of rats, but low doses of AA (0.5 mg/200 g) decreased this effect (16). These findings support my conclusion that AA serves as a zinc chelating agent, which is important for the regulation of intestinal zinc transport in both normal and diabetic rats. I have found that the optimal concentration of AA required to provide improved blood glucose levels of streptozotocin induced diabetic rats, was 11 mg/day/kg (69), 2.0 mg/day/kg for obese mice (70) and 4.0 mg/day/kg for diabetic G-K rats (71). Considering obese mice are more than twice as heavy as lean mice, doses of AA were similar to lean G-K diabetic rats based on lean body mass. AA treatment significantly reduced water intake in streptozotocin-induced diabetic rats (31,69), genetically obese mice (70), and diabetic G-K rats (71). Reduced water and food intake are signs of improvement in diabetes and obesity, respectively.

Experimental Data

The obesity activities of ZA and/or ZC were observed in five different rodent models: 1) streptozotocin-induced diabetic rats (Type 1 model), 2) ob/ob mice (Type 2 diabetes with obesity), 3) G-K rats (Type 2 diabetes without obesity), 4) aging rats (obese pre-diabetic), 5) high fat fed rats (diet-induced insulin resistance and weight gain), and 6) aged overweight S-D rats. These animal models mimic the diverse etiopathogenesis of human obesity and diabetes.

My preliminary data demonstrated that ZA and/or ZC treatments significantly reduced water and food intake in these rodent models. Since most of these improved clinical symptoms in rodents are signs of improved weight control, ZA and/or ZC may significantly down-regulate obesity in animal models. Correcting the clinical features of obesity in aged obese rats mimics the treatment in human obesity. Since these rodents eventually develop obesity in the aging process, ZA and/or ZC apparently has tremendous potential to treat human obesity, which is associated with leptin resistance.

The unique characteristic of ZA and/or ZC is that they exhibit no apparent side effects, and it is easy to treat patients with high compliance. Therefore, I generated the data needed to validate that ZA and/or ZC are novel anti-obesity/overweight agents for the prevention and treatment of human obesity and overweight.

The results of my experiments are outlined in the following sections. Analysis of variance (ANOVA) method was used when determining P-values for multiple test groups. Paired t-test was used for comparison of the results of post-treatment to those of pretreatment. The statistical analysis was carried out using statistical analysis software. A p-value less than 0.05 was considered statistically significant.

Experimental Results Showing that CHP Reduces Body Weight

When 10-month old G-K rats were treated with 10 mg/L zinc with and without 1.0 mg/L CHP for 3 weeks, body weights in zinc alone and zinc plus CHP treated rats significantly decreased compared to controls (FIG. 1). However, the growth rates of one month old G-K rats were not affected by zinc or zinc plus CHP treatments (FIG. 2). CHP plus zinc treatment also decreased body weight gain in sucrose-induced overweight mice (FIG. 3) and in young ob/ob mice (Table 1). Aged Sprague-Dawley rats weighing over 500 g for female and 800 g for male reduced body weight more than 60 g/month (FIG. 4). However, when the rats become about 370 g for female or 600 g for male, no further body weight loss was observed. In addition, lean aged rats did not lose body weight by the treatment with zinc plus CHP. Without wishing to be bound by any theory, I believe that CHP plus zinc improves "leptin resistance", which is considered the main cause of overweight and obesity, or an impaired response to leptin signaling in the hypothalamic leptin receptor, which inhibits NPY synthesis (50). NPY causes obesity by increasing appetite and food intake. Although the mechanisms are not clear, I have observed that both ZC and ZA reduced body weight or growth rate in aged diabetic G-K rats, aged overweight Sprague-Dawley rats, sucrose fed aged overweight C57B1/6J mice (FIGS. 1–5, Table 1).

TABLE 1

Effects of increasing doses of cyclo-Hispro (CHP) treatment for 21 days on body weight gain, water intake and food intake.[a]

| CHP[b] (mg/L) | Group[c] | Body Weight Gain (g) | Water Intake (ml/kg BW/day) | Food Intake (g/kg BW/day) |
|---|---|---|---|---|
| 0 | Lean | 1.0 ± 0.9 | 236.9 ± 43.8 | 159.0 ± 8.5 |
|   | Ob/ob | 3.5 ± 0.3 | 179.6 ± 16.4 | 119.6 ± 9.4 |
| 0.5 | Lean | 1.5 ± 0.4 | 267.1 ± 22.7 | 171.7 ± 12.5 |
|   | Ob/ob | 4.3 ± 0.8 | 198.2 ± 13.5 | 128.3 ± 7.8 |
| 1.0 | Lean | 1.3 ± 0.5 | 258.2 ± 21.8 | 159.6 ± 7.3 |
|   | Ob/ob | 2.3 ± 0.8* | 160.4 ± 9.7 | 110.6 ± 10.3 |
| 1.5 | Lean | 2.2 ± 0.9 | 302.5 ± 27.2 | 180.6 ± 19.5 |
|   | Ob/ob | 3.8 ± 0.9 | 192.5 ± 16.8 | 120.7 ± 10.4 |

[a]Values are mean ± SEM
[b]Each treatment consisted of a given level of CHP plus 10 mg/L of zinc and 0.5 mg/L of L-histidine.
[c]Each group contained four mice.
*p < 0.05 compared to 0 or 0.5 mg CHP/L group in ob/ob mice (ANOVA multiple comparison)

Hyperinsulinemia is one of the major pathological conditions of obesity because insulin stimulates food intake and lipid accumulation in fat tissues. I have found that increasing doses of CHP decreased plasma insulin levels in young hyperinsulinemic diabetic G-K rats. I believe that decreased plasma insulin levels helps to reduce body weight because insulin increases fat deposition.

EXAMPLE 1

Lone-Term ZC Treatment Effects on Plasma Insulin Levels in G-K Rats 6-month old G-K rats were treated with DW, 10 mg/L zinc, 1.0 mg/L CHP, or 10 mg/L zinc plus 0.25, 0.5, or 1.0 mg/L CHP. Plasma insulin levels of G-K rats treated with low dose CHP (0.25 mg/L) plus 10 mg/L zinc were significantly higher than in controls (treated with distilled water only). However, higher doses of CHP decreased plasma insulin levels. (Table 2)

Table 2: Plasma Insulin Levels in 6-Month Old G-K Rats Treated with Various Doses of Zinc and CHP

| Levels of Zinc and CHP in Drinking Water (mg/L) | Plasma Insulin Levels (ng/Ml) (mean ± SEM) | p-values* compared to DW only | p-values* compared to CHP only |
|---|---|---|---|
| DW | 0.457 ± 0.025 | — | <0.01 |
| Zinc only (10 mg/L) | 0.637 ± 0.048 | <0.05 | <0.05 |
| CHP only (1.0 mg/L) | 0.907 ± 0.090 | <0.01 | — |
| Zinc plus CHP (10/0.25 mg/L) | 0.817 ± 0.167 | <0.01 | NS |
| Zinc plus CHP (10/0.5 mg/L) | 0.621 ± 0.079 | <0.05 | <0.05 |
| Zinc plus CHP (10/1.0 mg/L) | 0.552 ± 0.092 | NS | <0.01 |

*T-tests were used to compare the values to the DW only and CHP only treated rats.

Anti-Hyperphagia Activities of CHP:

CHP causes reduced intake of food (62,63, 69–73). Hyperphagia is considered to be the most important contributor in developing obesity. Food intake in 10 month old G-K rats significantly decreased with ZC treatment, but not in 1 month old rats (FIG. 6). Sucrose intake was also reduced in 32% sucrose solution treated overweight 8 month old C57B1/6J mice (FIG. 7). This data indicates that ZC exhibits anti-obesity activities in aged rats without affecting young rats.

EXAMPLE 2

ZA/ZC Treatment Decreases Food and Water Intake in Obese ob/ob Mice

Eight week old male C57BL/6J-obese ob/ob mice and their lean wild-type littermates were randomly divided into five groups of mice and treated with the following levels of AA in drinking water: (i) 0 mg AA/l; (ii) 10 mg AA/l; (iii) 20 mg AA/l; (iv) 50 mg AA/l; or (v) 100 mg AA/l. 10 mg zinc and 0.5 mg L-histidine/l were also included at each level of AA described above. The treatment solutions were replaced with freshly prepared solutions every other day during the 2-week treatment period. Body weight, and food and water intake were measured every other day in the morning, beginning the first day of treatment.

Water intake in obese mice treated with 20, 50 or 100 mg AA/l were significantly lower than those given only zinc and L-histidine (p<0.05). Food intake in obese mice treated with 20 mg/L AA plus zinc was significantly lower than those treated with only zinc and L-histidine (p<0.05). (Table 3). There was no treatment effect on water and food intake in lean mice. There was also no effect of treatment on body weight in either obese or lean mice.

TABLE 3

Effects of arachidonic acid and zinc treatment for 14 days on water intake, food intake, and body weight gain.[a]

| AA[b] (mg/L) | Group[c] | Water Intake (ml/kg BW/day) | Food Intake (g/kg BW/day) | Body Weight Gain (g) |
|---|---|---|---|---|
| 0 | Lean | 221.1 ± 22.5 | 135.7 ± 9.3 | 0.8 ± 0.4 |
|   | Ob/ob | 227.0 ± 13.2 | 132.5 ± 10.1 | 2.4 ± 0.1 |
| 10 | Lean | 207.3 ± 23.6 | 143.9 ± 13.2 | 1.0 ± 0.2 |
|   | Ob/ob | 215.9 ± 15.2 | 126.5 ± 13.2 | 2.3 ± 0.7 |
| 20 | Lean | 211.6 ± 23.6 | 129.9 ± 11.1 | 0.6 ± 0.2 |
|   | Ob/ob | 182.9 ± 12.4* | 107.5 ± 9.0* | 2.6 ± 0.4 |
| 50 | Lean | 211.9 ± 21.5 | 133.1 ± 9.5 | 1.0 ± 0.3 |
|   | Ob/ob | 188.7 ± 11.5* | 114.4 ± 9.9 | 2.4 ± 1.7 |
| 100 | Lean | 216.1 ± 21.0 | 130.0 ± 13.2 | 0.6 ± 0.1 |
|   | Ob/ob | 198.9 ± 15.3* | 116.0 ± 12.0 | 2.9 ± 0.5 |

[a]Values are mean ± SEM
[b]Each treatment consisted of a given level of AA plus 10 mg/L of zinc and 0.5 mg/L of L-histidine.
[c]Each group contained five mice.
*p < 0.05 compared to 0 mg/l group.

Anti-polydipsia Activities of CHP and Arachidonic Acid:

Water intake in 10 month old G-K rats was significantly lower when treated with zinc or ZC compared to distilled water (DW) treated rats (P<0.01) (FIG. 8). Polydipsia is often associated with diabetes (69–73) and obesity (74,75). Similar to body weight control, water intake in 1.0-month-old rats was not affected (reduced) by treatment with Zn or ZC. However, water intake was not reduced to below normal levels and aged rats did not develop dehydration. Although body weight changes in 8-month old S-D rats were slightly affected by the treatment with zinc or ZC (FIG. 5), water intakes were significantly decreased by the treatment with zinc or ZC in these S-D rats (FIG. 9). Treatment with CHP plus zinc in Ob/ob mice also reduced water intake (69–73, Table 1). This data supports my conclusion that CHP treatment improves polydipsia in old obese rats without affecting normal young rats. Water intake also decreased in aged G-K rats treated with ZA (FIG. 10). Similar to CHP treatment, higher doses of AA significantly decreased water consumption rates in diabetic rats (69–73). Without being bound by any theory, I interpret this data to mean that both AA and CHP may improve body weight control by reducing polydipsia, or satiety control mechanisms that are directly or indirectly related to the water intake control center in the hypothalamus (74,75), affecting the pathophysiology of obesity and diabetes.

EXAMPLE 3

Water Intake in G-K Rats Treated with AA Plus Zinc

One-month old G-K rats were treated with either distilled water (DW) only, 10 mg/L zinc only, 20 mg/L AA only, or increasing levels of AA (10, 20 or 30 mg/L) plus 1.0 mg zinc and 0.5 mg L-histidine/L for 2 weeks. Water intake was decreased most in rats treated with either 20 or 30 mg/L AA plus 10 mg/L zinc. The rats treated with either 10 mg/L zinc only or 10 mg/L AA plus 10 mg/L zinc also significantly decreased water intake. (FIG. 10). Thus, water intake was reduced in rats with all treatments containing zinc relative to DW-treated rats, but not with the AA-only treatment.

EXAMPLE 4

Long-Term ZC Treatment Effects on Water Intake in G-K Rats

Six-week old G-K rats were divided into six groups of 5–10 rats and treated with distilled water (DW) only, 10 mg/L zinc only, 1.0 mg/L CHP only, 10 mg/L zinc plus 0.25, 0.5, or 1.0 mg/L CHP for two weeks. The amount of water intake was measured every 2–3 days. Water intake significantly decreased in diabetic G-K rats treated only with 1.0 mg CHP/L (0.15 mg CHP/Kg BW/day) plus 10 mg/L zinc (1.5 mg zinc/kg BW/day), compared to the value obtained from DW-treated rats.

The Effects of ZC and/or ZA on the Growth Rate of Rats and Mice

Although decreased body weights, and food and water intake were exhibited in aged diabetic rats and mice (FIGS. 1–10, Table 1), body weight growth in 1.0 month old G-K rats was not affected (FIG. 1). However, when male G-K rats were 1.5 month olds or weighed about 200 g, the growth rate treated with ZC significantly decreased (FIG. 11). When both 3 month old male and female G-K rats were treated with ZC for more than two weeks and ceased treatment for another two weeks, ZC treated rats decreased growth rate compared to distilled water (DW) or Zinc only treated rats (FIGS. 12, 13). I believe that CHP is effective in maintaining body weight control even after the cessation of the treatment.

EXAMPLE 5

ZC Treatment Decreases Body Weight Gain in ob/ob Mice

Ob/ob and lean mice were randomly divided into four groups and treated with drinking water containing either 0, 0.5, 1.0, or 1.5 mg CHP/L plus 10 mg zinc and 0.5 mg L-histidine/L. Drinking water containing test substances was prepared every other day with freshly prepared solutions. During the testing non-fasting blood glucose concentrations, food and water intake, and body weight were measured every other day in the morning. Non-fasting plasma insulin concentrations and three-hour average blood glucose concentrations were determined at the end of the three-week treatment period.

Body weight gain was significantly reduced in ob/ob mice treated with 1.0 mg CHP/L plus zinc and L-histidine relative to those given zinc and L-histidine only (P<0.05) (Table 1). Water and food intake was lowest in ob/ob mice treated with 1.0 mg CHP plus zinc and L-histidine, however this difference was not significant relative to the other treatment groups (0, 0.5, or 1.5 mg CHP/L) (Table 1).

Without being bound to any theory, I believe that this data (FIGS. 1–13, Table 1) supports my conclusion that zinc and CHP are synergistically effective in the control of glucose utilization and body weight control in age-releated hyperinsulinemia and obesity. More importantly, I believe that this preliminary data (FIGS. 1–13, Table 1) and published literature (69–73) supports my conclusion that ZA and/or ZC improves leptin-resistance associated with obesity.

From this preliminary data, I have made several observations. First, the growth rate of young rats increased, but body weight in old rats decreased with ZA and/or ZC treatment. This suggests that certain metabolic factors are adjusted by ZA and/or ZC treatment in aged obese rats to maintain normal body weight, and that ZA and/or ZC consumption by young normal subjects are safe and could be beneficial.

Second, the intake of water and food were invariably decreased with ZA and/or ZC treatments. Since polydipsia and polyphagia are characteristics of obesity and diabetes, ZA and/or ZC clearly improves these clinical signs of obesity.

Third, ZA and ZC improved oral glucose tolerance in aged overweight pre-diabetic and genetically diabetic G-K rats, and genetically obese ob/ob mice without effecting young normal rats. Since plasma insulin levels decreased or did not change with ZA and/or ZC treatments, I interpret this data to mean that ZA and/or ZC primarily stimulates peripheral tissue glucose utilization, rather than insulin secretion.

Fourth, fasting and postprandial blood glucose levels decreased with ZA and/or ZC treatments in all the diabetic and obese animals. These results support my previous conclusion that ZA and/or ZC stimulate insulin action on liver and muscle tissues, since streptozotocin-treated rats cannot be treated with insulin secretion stimulation.

Finally, optimal doses of ZA and/or ZC are variable, depending on the type of treatment and animal models. The most effective doses of ZA and/or ZC for acute treatment of overweight mammals are 5 times higher than that for chronic treatment. ZA and/or ZC doses for obese mammals can be up to 3 times higher than for non-obese, but overweight mammals. Based on lean body mass, ob/ob mice require similar doses of AA or CHP to non-obese G-K rats in the control of blood glucose levels.

In conclusion, I have found that zinc, CHP, and AA synergistically affect glucose utilization in muscle and fat tissues (69–73), and control body weight (FIGS. 1,3–5, 11–13, Table 1), possibly ameliorating hypothalamic leptin resistance. Zinc stimulates both insulin synthesis in rats (76) and leptin synthesis in humans (77). Zinc is known to be involved with insulin receptor-mediated signal transduction mechanisms to increase glucose uptake in muscle cells and adipocytes (39,40). Human obesity is characterized by leptin resistance in hypothalamus (50). I have demonstrated that all the rats and mice treated with ZA and/or ZC had significantly reduced intake of water and food (FIGS. 6–10), and old animals lost weight (FIG. 4) and reduced weight gains in sucrose-induced overweight mice (FIG. 3). This supports my conclusion that ZA and/or ZC are strong anti-obesity agents. Although the mechanisms by which ZA and/or ZC control food and water intake through hypothalamic signaling systems are essentially unstudied, increased food intake is the major characteristic of obesity. Therefore I believe that ZA and/or ZC treatment reduces body weight and food intake in aged overweight/obese rats, and that ZA and/or ZC are excellent anti-obesity agents for the prevention and treatment of human obesity and overweight.

Preparation of CHP Containing SPH

In one preferred embodiment, CHP treatment comprises consuming a soybean protein hydrolysate (SPH), wherein the SPH comprises an enriched mixture of CHP and various other peptides. The SPH can be consumed alone or added to a variety of foods. These foods include, but are not limited to, protein shakes, meal replacement or energy bars, snack foods and the like. In another embodiment, zinc is added to the CHP containing SPH. In order to maximize the amount of CHP in the SPH the following methods may be utilized.

The first step is the preparation of a CHP containing soybean protein hydrolysate (SPH). This is done by temperature manipulation in two soybean protein hydrolyzing methods (acid and alkaline hydrolysis).

The preferred method of producing the SPH preparations is to hydrolyze soybean protein in either acid or alkaline solution followed by refluxing in the presence of an alcohol/carbonate solution. In one embodiment the alcohol carbonate solution is $KHCO_3/EtOH$. Hydrolysis of soybean protein is a simple standard method. The detailed procedure for obtaining optimal amounts of the dipeptide L-histidyl-proline can be readily determined by those skilled in the art through the techniques of the present study. Too much hydrolysis may result in lost dipeptides and too weak hydrolysis produces low yield of L-histidyl-proline in the soybean protein hydrolysate.

Once the method to obtain the maximum amount of L-histidyl-proline has been determined, the method of converting dipeptide to CHP can be done easily with more than 90% yield. It has been known that higher temperatures produce high yields of CHP (78). Thus, the duration of autoclaving and heating the final preparation at different temperatures may affect the yield of L-histidyl-proline dipeptide and CHP. I expect to see different amounts of CHP in different length of autoclave cycles, heating temperatures, and duration of heating of the final product. For example, the following parameters can be tested in order to optimize the amount of CHP in the SPH:

|  | Protein Sample | | | | | | | |
|---|---|---|---|---|---|---|---|---|
| Step 1: Hydrolysis Method | Acid Hydrolysis | | | | Alkaline Hydrolysis | | | |
| Step 2: Length of Autoclave (hours) | 1 | 5 | 10 | 15 | 1 | 5 | 10 | 15 |
| Step 3: Heating Temperature (° C.) | 25 | 37 | 65 | 100 | 25 | 37 | 65 | 100 |
| Step 4: Length of Heating (hours) | 1 | 5 | 10 | 15 | 1 | 5 | 10 | 15 |

For example, using the acid hydrolysis method, the samples may be autoclaved for 5 hours and then heated at 100° C. for 1 hour.

Using standard acid and alkaline hydrolysis methods, and established method to convert L-histidyl-proline to CHP, different SPH preparations will be made as shown below.

Method A: Soybean Protein Hydrolysate (SPH) Preparation by Acid Hydrolysis Procedure
1. Ten ml of 8 N $H_2SO_4$ was added to 1 g of soybean protein in a 100-ml Erlenmeyer flask. Each flask was labeled and sealed with cotton.
2. The flasks were then autoclaved at 15 lbs for 1, 5, 10, 15 hrs. The physical appearance of each sample was recorded.
3. After the autoclave procedure was complete, the hydrolysates were neutralized with barium hydroxide. In order to neutralize 10 ml of 8 N $H_2SO_4$ a total of 80.8 grams of barium hydroxide [$Ba(OH)_2.8H_2O$] were added. Approximately 70 grams were added as solid $Ba(OH)_2.8H_2O$. This was followed by the addition of a saturated barium hydroxide solution which was used to bring the solution to pH 7.0.
4. The resulting voluminous white precipitate was removed by centrifugation at 1000×g for 15 minutes, washed twice with 10 ml of boiling distilled water, and discarded.
5. The final solution was heated at 25, 37, 65, or 100° C. for 1, 5, 10, or 15 hours.
6. The combined supernatant and washing water was then brought to a 50 ml total volume. This preparation was subsequently used to convert the L-histidyl-proline dipeptide in the SPH to CHP.

Method B: Soybean Protein Hydrolysate (SPH) Preparation by Alkaline Hydrolysis Procedure
1. 1 g of soybean protein was added to a 100-ml Erlenmeyer flask, followed by the addition of 10 ml of boiling water and 12.72 g $Ba(OH)_2.8H_2O$. Each flask was then labeled and sealed with cotton.
2. The flasks were warmed gently while mixing to dissolve most of the $Ba(OH)_2$ and autoclaved at 15 lbs. for 1, 5, 10, or 15 hrs. Physical appearance of each sample was recorded.
3. The hydrolysates were brought to pH 10 using 16 N $H_2SO_4$. For the final neutralization to pH 7.0, 1.0 N $H_2SO_4$ solution was used.
4. The resulting voluminous precipitate was removed by centrifugation at 1000×g for 15 minutes, washed twice with 10 ml of boiling distilled water, and discarded.
5. The final solution was heated at 25, 37, 65, or 100° C. for 1, 5, 10, or 15 hours.
6. The combined supernatant and washing water was then brought up to 50 ml total volume. This preparation was subsequently used to convert the L-histidyl-proline dipeptide in the SPH to CHP.

Method C: Chemical Synthesis of Cyclo-Hispro (CHP) from the Soybean Protein Hydrolysate (SPH)

The final step of preparing CHP is done by refluxing the preferred preparation of SPH in the presence of EtOH/$KHCO_3$. The preferred SPH preparation obtained from either acid or alkaline hydrolysis methods (Method A or B), based on the CHP content, can be used as the starting material. CHP concentration will be determined by radio immune assay (RIA) method using RIA kit to be supplied by American Peptide Co. (Sunnyvale, Calif.). The yield of CHP obtained by refluxing the L-histidyl-proline in the SPH prepared by hydrolysis method is greater than 90%. The preferred preparation of SPH with the hydrolysis method contains substantial amounts of L-histidyl-proline, and refluxing this SPH will yield the highest amount of CHP in the SPH. Thus, results from the method of chemical synthesis of CHP from SPH prepared by hydrolysis method allows production of the maximal amounts of CHP in the hydrolysate. However, if any one of the protein hydrolysate preparations described above show almost the same amount of CHP prepared by the refluxing method, then the preparation of SPH containing the highest amount of CHP can be used for the commercialization without undergoing refluxing.

LITERATURE REFERENCES

1. Flegal K M, Carroll M D, Kuczmarski R J, Johnson C L. Overweight and obesity in the United States: Prevalence and trends, 1960–1994. Int J Obes 22:39–47, 1998.
2. Chaganon Y C, Perusse L, Bouchard. The human obesity gene map: the 1997 update. Obes Res 6:76–92, 1998.
3. Zhang Y Y, Proenca R, Mafei M. et al. Positional cloning of the mouse obese gene and its human homologue. Nature 372:425–432,1994.
4. Montague C T, Farooqui I S, Whitehead J P et al. Congenital leptin deficiency is associated with severe early-onset obesity in human. Nature 387: 903–908, 1997.
5. Prasad C, Mizuma H, Brock J W, Porter J R, Svec F, Hilton C. A paradoxical elevation of brain cyclo (his-pro) levels in hyperphagic obese Zucker rats. Brain Res 699: 149–153, 1995.
6. Halaas J L, Gajiwala K S, Maffeei M Cohen S L, Chalt B T, Rabinnnnowitz D, Lallone R L, Burley S K, Friedman J M. Weight-reducing effects of the plasma protein encoded by the obese gene. Science 269:543–546, 1995.
7. Schwartz M W, Seeley R J, Campfield L A, Burn P, Baskin D G. Identification of targets of leptin action in rat hypothalamus J Clin Invest 98:1101–1106, 1996.
8. Levine A S, Morley J E. Neuropeptide Y: a potent inducer of consummatory behavior in rats. Peptides 5:1025–1029, 1984.
9. Considine R V, Sinha M K, Heiman M I, Kriauciunas A, Stephens T W, Nyce M R, Ohannesian J P, Marco C C, McKee, L J, Bauer T L, Caro J F. Serum immunoreactive-leptin concentrations in normal weight and obese humans. N Engl J Med 334:292–295, 1996.
10. Bouchard C, Trembaly A, Despress J P, et al. The response to long-term overfeeding in identical twins. N Engl J Med 322: 1477–1482, 1990.
11. Fried S K, Russel C D: Diverse roles of adipose tissue in the regulation of systemic metabolism and energy balance. In: Bray G A, Bouchard C, James W P, eds. Handbook of Obesity. New York, Marcel Dekker, 1977. pp 397–414.
12. Connolly H M, Crary J L, McGoon M D et al. Valvular heart disease associated with fenfluramine-phentermine New Engl J Med 337:581–588, 1997.
13. Bray G A, Inoue S. Pharmacological treatment of obesity. Am J Clin Nutr 55:151S–319S, 1992.
14. Mantozoros C S, Prasad A S, Beck F W J, Grabowski S, Kaplan J. Adair C, Brewer G J. Zinc may regulate serum leptin concentrations in humans J Am Coll. Nutr 17:270–275, 1998.
15. Song M K, Adham N F: The role of prostaglandin E2 in zinc absorption in the rat. Am J Physiol 234:E99-E105, 1978.
16. Song M K, Littner M R, Adham N F, Kazmi G M, Lott F D: Effect of oral administration of arachidonic acid on prostaglandin and zinc metabolism in plasma and small intestine of the rat. Pros Leuko Med 17:159–166, 1984.
17. Rosenthal M J, Hwang I K, Song M K: Effects of arachidonic acid and cyclo(his-pro) on zinc transport across small intestine and muscle tissues. Life Sci. 70:337–348, 2001.
18. Kow L M, Pfaff D W. Cyclo (his-pro) potentiates the reduction of food intake induced by amphetamine, fenfluramine, or serotonin. Pharamcol Biochem Behav 38:365–369,1991.
19. Caro J F, Kolaczynski J W, Nyce M R, Ohannesian J P et al. Decreased cerebrospinal fluid/serum leptin ratio in obesity: a possible mechanisms for leptin resistance. Lancet 348:159–161, 1996.
20. Van Heek M, Compton D S, France C F, Tedesco R P, Fawzi A B, et al. Diet-induced obese mice develop peripheral, but not central, resistance to leptin. J Clin Invest 99:385–390, 1997.
21. Faclchuk K H, Fawcett D W, Valle B L. Role of zinc in cell division of *Euglena gracilis*. J Cell Sci 17:57–78, 1975.
22. Song M K, Kim Y Y, Heng M C Y, Adham N F and Ament M E: Prostaglandin interacts with steroid sex hormones in the regulation of intestinal zinc transport. Comp Biochem Physiol 101A: 477–481, 1992.
23. Pham R, Kim Y Y, Song M K, Heng M C Y. Factors affecting zinc flux rates of rat intestinal segments mounted into Ussing chambers. Biochem. Arch 7:213–219, 1991.
24. Hurley L S, Lonnerdal B, Stanislowski A G: Zinc citrate, human milk, and *acrodermatitis enteropathica*. The Lancet I: 677, 1979.
25. Von Euler U S. Zur Kenntnis der pharmakologischen Wirkungen von Nativsekreten und Extrakten mannlicher accessorischer Geschlechtsdreisen. Arch exp Path Pharamak 175:78–84, 1934.
26. Halstead J A, Smith J C Jr., Irwin M I. A conspectus of research of zinc requirements of man. J Nutr. 104:345–349, 1974
27. Arver S: Zinc and zinc ligands in human seminal plasma. III. the principal low molecular weight zinc ligand in prostatic secretion and seminal plasma. Acta Physiol Scand 116:67–73, 1982.
28. Belanger B, Belanger A, Labrie F. et al.: Comparison of residual C-19 steroid in plasma, and prostatic tissues of human, rat and guinea pig after castration: Unique importance of extratesticular androgens in men. J Steroid Biochem 32:695–698, 1989.
29. Pekary A E, Sharp B, Briggs J, Carlson H E, Herschman J M. High concentrations of p-Glu-His-Pro-NH$_2$ (Thyrotrophin-releasing hormone) occur in rat prostate. Peptides 4:915–919, 1983.
30. Fushimi H, Horie H, Inoue T, Kameyama M, Ishihara S, Tsujimura T, Nunotani H, Minami T: Low testosterone levels in diabetic men and animals: A possible role in testicular impotence. Diabet Res Clin Pract 6:297–301, 1989.
31. Song M K, Adham N F, Rosenthal M, Mooradian A D, Ament M E: Effects of animal prostate extract on zinc metabolism in diabetic rats. Diabet Res 31:157–170, 1996.
32. Song M K, Mooradian A D: Intestinal zinc transport: Influence of streptozotocin-induced diabetes, insulin and arachidonic acid. Life Sci 42:687–694, 1988.
33. Kinlaw W B, Levine A S, Moreley J E, Silvis S E, McClain C J: Abnormal zinc metabolism in Type II diabetes mellitus. Am J Med 75:273–77, 1983.

34. Gochishan F K, Green H L: Intestinal transport of zinc in the diabetic rat. Life Sci 32:1735–41, 1983.
35. Johnson W T, Canfield W K: Intestinal absorption and excretion of zinc in streptozotocin-diabetic rats as affected by dietary zinc and protein. J Nutr 115:1217–27, 1985.
36. Killrich S, Huid-Jacobsen K, Vaag A, Sorensen S S: $^{65}$Zn absorption in patients with insulin-dependent diabetes mellitus assessed by whole-body counting technique. Clin. Chim. Acta 189:13–18, 1990.
37. Levine A S, McClain C J, Handwerger B S, Brown D M, Moreley J E: Tissue zinc status of genetically diabetic and streptozotocin-induced diabetic mice. Am J Clin Nutr 37:382–386, 1983.
38. Chooi M K, Todd J K, Boyd N D: Influence of age and sex on plasma zinc levels in normal and diabetic individuals. Nutr Metab 20:135–142, 1976.
39. Ezaki O: IIb group metal ions ($Zn^{2+}$, $Cd^{2+}$, $Hg^{2+}$) stimulate glucose transport activity by post-insulin receptor kinase mechanism in rat adipocytes. J Biol Chem 264:16118–16122, 1989.
40. Tang X-H, Shay N F. Zinc has an insulin-like effect on glucose transport mediated by phosphoinositol-3-kinase and AKT in 3 T#-L1 fibroblasts and adipocytes. J Nutr 131:1414–1420, 2001.
41. Mangian H F, Lee R G, Paul G L, Emmert J L, Shay N F. Zinc deficiency suppresses plasma leptin concentration in rats. J Nutr. Biochem. 9:47–51. 1998.
42. Mantzoro C S, Prasad A S, Beck F W J, Crabowski S, Kaplan J. Adair C, Brewer G J. Zinc may regulate serum leptin concentrations in humans. J Am Coll Nutr 17:270–275, 1998.
43. Chen M D, Song, Y M, Lin P Y. Zinc may be mediator of leptin production in humans. Life Sci 66:2143–2149, 2000.
44. Chen M D, Lin P Y. Zinc-induced hyperleptinemia relates to the amelioration of sucrose-induced obesity with zinc repletion. Obes Res 8:525–529, 2000.
45. Bock B C, Kanarek R B, Aprille J R. Mineral content of the diet alters sucrose induced obesity in rats. Physiol Behav 57:659–668, 1995.
46. Di Martino G, Martera M G, DeMartino B, Vacca C, DiMartino S, Rossi F. Relationship between zinc and obesity. J Med 24:177–183, 1993
47. Lee R G, Rains T M, Tovar-Palacio C, Beverley J L, Shay N F. Zinc deficiency increases hypothalamic neuropeptide Y and neuropeptide Y mRNA levels and does not block neuropeptide Y-induced feeding in rats. J Nutr 128:1218–1223, 1998.
48. Taneja S K, Mahajan M, Arya P. Excess bioavailability of zinc may cause obesity in humans. Experientia 52:31–33, 1996.
49. Chen M D, Liou S J, Lin P Y, Yang V C, Alexanders P S, Lin W H. Effects of zinc supplementation on the plasma glucose level and insulin activity in genetically obese (ob/ob) mice. Biol Trace Elem Res 61:303–311, 1998.
50. Scarpace P J, Matheny M, Tumer N. Hypothalamic leptin resistance is associated with impaired leptin signal transduction in aged obese rats. Neuroscience 104:1111–1117, 2001.
51. Phinney S D, Davis P G, Johnson S B Holman R T. Obesity and weight loss alter polyunsaturated lipid metabolism in humans. Am J Clin Nutr 51:831–838, 1991.
52. Guesnet P, Boune J M, Pascal G, et al. Tissue phospholipid fatty acid composition in genetically lean and obese Zucker female rats on the same diet. Lipids 25:517–522, 1990.
53. Wahle K W, Milne L, McIntosh G. Regulation of polyunsaturated fatty acid metabolism in tissue phsopholipids of obese (fa/fa) and lean (Fa/-) Zucker rats. I. Effect of dietary lipids on cardiac tissues. Lipids 26:16–22, 1991.
54. Phinney S D, Tang A B, Thurmond D C, Nakamura M T, Stem J S. Abnormal polyunsaturated lipid metabolism in the obese Zucker rat, with partial metabolic correction by γ-linolenic acid administration. Metabolism 42:1127–1140, 1993.
55. Loftus T M, Jaworsky D E, Frehywort G L, Townsend C A, Ronnet G V, Lane M D, Kuhajda F P. Reduced food intake and body weight in mice treated with fatty acid synthase inhibitors. Science 288:2379–2381, 2000.
56. Doggett N S, Jawaharlal K. Anorectic activity of prostaglandin precursors. Brit J Pharmacol 60:417–423, 1977.
57. Reginanato M J, Krakow S L, Bailey S T, Lazar M A. Prostaglandins promote and block adipogenesis through opposing effects on peroxisome proliferator-activated receptor gamma. J Biol Chem 273:1855–1858, 1998.
58. Borza D B, Morgan W T. Histidine-proline-rich glycoprotein as plasma pH sensor. J Biol Chem 273:5493–5499, 1998.
59. Morgan W T. Human serum histidine-proline-rich glycoprotein. Biochim Biophys Acta 533:319–333, 1978.
60. Hilton C W, Prasad R C, Vo P, Mouton C. Food contains the bioactive peptide, cyclo (his-pro). J Clin Endocrinol Metab 75:375–378, 1992.
61. Mizuma H, Legardeur B Y, Prasad C, Hilton C. The bioactive peptide cylco (his-pro) may be absorbed following ingestion of nutritional supplements that contain it. J Am coll Nutr 15:175–179, 1996.
62. Morley J E, Levine A S, Prasad C. Histidyl-proline diketopiperazine decreases food intake in rats. Brain Res. 210:475–478, 1981.
63. Steiner J H, Wilber J F, Prasad C, Rogers D, Rosenkranz R T. Histidyl proline diketopiperazine (cyclo [his-pro]) in eating disorders. Neuropeptides 14:185–189, 1989.
64. Prasad C, Mizuma H, Brock J W, Porter J R, Svec F, Hilton C. A paradoxical elevation of brain cyclo (his-pro) levels in hyperphargic obese Zucker rats. Brain Res 699:149–153, 1995.
65. Ishihara H, Mori M, Kobayashi I, Kobayashi S. Intraventricular administration of cyclo (his-pro), metabolite of thryrotrophin-releasing hormone (TRH), decreases water intake in the rat. Proc Soc Exp Biol Med 178:623–628, 1985.
66. Kelts K A, Hoehn M M. Hypothalamic atrophy. J Clin Psychiatry 39:357–358, 1978
67. Eckersley G N, Gell J K, Kriek N P. A craniopharyngioma in a seven-year-old dog. J S Afr Vet Assoc 62:65–67, 1991.
68. Serdula M K, Mokdad A H, Williamson D F, Galuska D A, Mendelein J M, Heath G W. Prevalence of attempting weight loss and strategies for controlling weight. JAMA 282:1353–1358, 1999.
69. Song M K, Rosenthal M J, Hong S J, Hwang I K, Yip I, Golub, M S, Ament M E, Go, V L W. Synergistic anti-diabetic activities of zinc, cyclo (his-pro) and arachidonic acid. Metabolism 50:53–59, 2001
70. Hwang I K, Go, V L W, Harris D M, Yip I, Song, M K. Effects of arachidonic acid plus zinc on glucose disposal in genetically diabetic (ob/ob) mice. Diabet Obes Metabol 4:124–131, 2002
71. Song M K, Hwang I K, Rosenthal M J, Harris D M, Yamaguchi D T, Yip I, Go, V L W. Anti-diabetic actions of arachidonic acid and zinc in genetically diabetic Goto-Kakizaki rats. Metabolism In Press 2002.
72. Hwang I K, Kang K W, Harris D M, Yip I, Go V L W, Song M K. Effects of cyclo (his-pro) and zinc on clinical signs of diabetes in genetically obese (ob/ob) mice. Submitted for publication to Diabet Obes Metabol. 2002
73. Song M K, Hwang I K, Rosenthal M J, Harris D M, Yamguchi D T, Yip I, Go V L W. Anti-hyperglycemic activities of cyclo (his-pro) in genetically diabetic Goto-Kakizaki and aged rats. Submitted for publication to "Metabolsim".
74. Stookey J D. Energy density, energy intake and weight status in a large free-living sample of Chinese adults: exploring the underlying roles of fat, protein, carbohydrate, fiber and water intakes. Eur J Clin Nutr 55:349–359, 2001.
75. Durr J, Karakash C, Vallotton M B, Jeanreanud B. Abnormal water turnover associated with hypothalamic obesity. Endocrinology 108:1228–1232, 1981.
76. Chauser A B. Zinc, insulin and diabetes. J Am Coll Nutr 17:109–115, 1998.
77. Chen M D, Song Y M, Lin P Y. Zinc may be mediator of leptin production in humans. Life Sci. 66:2143–2149, 2000.
78. Hilton C W, Prasad C, Wilber J F, Svec F, Vo, P, Reddy S. Cylco (his-pro) in nutritional supplements. Lancet 336:1455, 1990.

What is claimed is:

1. A method of reducing body weight in an overweight or obese mammal, said method comprising:
    administering at least once daily to the overweight or obese mammal a pharmaceutical composition;
    wherein said pharmaceutical composition comprises:
      a zinc cation and an anion, and cyclo-Hispro
    wherein said zinc cation is administered to the mammal in an amount from about 0.01 to about 1.4 mg/kg/day; and
    wherein the cyclo-Hispro is administered to the mammal in an amount from about 0.007 to about 1.4 mg/kg/day.

2. The method of claim 1 wherein said cyclo-Hispro is administered to the mammal in an amount from about 0.1 to about 1 mg/kg/day.

3. The method of claim 1 wherein said cyclo-Hispro is administered to the mammal in an amount from about 0.007 to about 0.7 mg/kg/day.

4. The method of claim 3 wherein said cyclo-Hispro is administered to the mammal in an amount from about 0.07 to about 0.4 mg/kg/day.

5. The method of claim 1 wherein said zinc cation ranges is administered to the mammal in an amount from about 0.07 to about 0.7 mg/kg/day.

6. The method of claim 5 wherein said zinc cation is administered to the mammal in an amount from about 0.1 to about 0.4 mg/kg/day.

7. The method of claim 1 wherein said pharmaceutical composition further comprises L-histidine, wherein the L-histidine is administered to the mammal in an amount front about 0.001 to about 0.1 mg/kg/day.

8. The method of claim 1 wherein said pharmaceutical composition is administered two to four times daily.

9. The method of claim 1 wherein said pharmaceutical composition is formulated into a food or food supplement.

10. The method of claim 1 wherein said mammal also has hypertension and/or high cholesterol, wherein administering said composition also controls said hypertension and/or high cholesterol.

11. The method of claim 1 wherein the cyclo-Hispro is obtained from a soybean protein hydrolysate enriched for cyclo-Hispro.

12. The method of claim 11 wherein the hydrolysate has been prepared by a process comprising:
    hydrolyzing soybean protein into soybean protein hydrolysate using either acid or alkaline hydrolysis; and
    refluxing the soybean protein hydrolysate in the presence of an alcohol/carbonate mixture.

13. The method of claim 12 wherein the alcohol/carbonate mixture is $EtOH/KHCO_3$.

14. A method of reducing body weight in an overweight or obese mammal, said method comprising:
    administering at least once daily to the overweight or obese mammal a pharmaceutical composition;
    wherein said pharmaceutical composition comprises
      a zinc cation and anion; and arachidonic acid
    wherein said zinc cation is administered to the mamml in an maount from about 0.01 to about 1.4 mg/kg/day; and
    wherein said arachidonic acid is administered to the mammal in an amount from about 0.01 to about 14 mg/kg/day.

15. The method of claim 14 wherein said arachidonic acid is administered to the mammal in an amount from about 0.14 to about 10 mg/kg/day.

16. The method of claim 15 wherein said arachidonic acid is administered to the mammal in an amount from 0.3 to about 6 mg/kg/day.

17. The method of claim 16 wherein said ararhidonic acid is administered to the mammal in an amount from about 0.7 to about 4.3 mg/kg/day.

18. The method of claim 17 wherein said arachidonic acid is administered to the mammal in an amount of about 1.7 mg/kg/day.

19. The method of claim 14 wherein said zinc cation is administered to the mammal in an amount from about 0.07 to about 0.7 mg/kg/day.

20. The method of claim 14 wherein said pharmaceutical composition further comprises L-histidine, wherein the L-hisitidine is administed in an amount from about 0.001 to about 0.1 mg/kg/day L-histidine.

21. The method of claim 14, wherein said mammal also has hypertension and/or high cholesterol, wherein administering said composition also controls said hypertension and/or high cholesterol.

22. The method of claim 14 wherein said pharmaceutical composition is administered two to four times daily.

23. The method of claim 14 wherein said pharmaceutical composition is formulated into a food or food supplement.

24. The method of claim 14 wherein said zinc cation is administered to the mammal in an amount from about 0.1 to about 0.4 mg/kg/day.

* * * * *

UNITED STATES PATENT AND TRADEMARK OFFICE
CERTIFICATE OF CORRECTION

PATENT NO. : 7,144,865 B2
APPLICATION NO. : 10/768200
DATED : December 5, 2006
INVENTOR(S) : Moon K. Song It is certified that error appears in the above-identified patent and that said Letters Patent is hereby corrected as shown below:

On the Title page, column 2, (other publications), line 1, delete "Effect" and insert -- Effects --, therefor.

At column 11, line 67, after "2001)" insert -- . -- .

At column 12, line 12, delete "*I*" and insert -- I. --, therefor.

At column 18, line 17, delete "age-releated" and insert -- age-related --, therefor.

At column 20, line 19 (approx.), delete "[Ba(OH)$_2$.8H$_2$O]" and insert -- [Ba(OH)$_2$·8H$_2$O] --, therefor.

At column 20, line 20 (approx.), delete "Ba(OH)$_2$.8H$_2$O." and insert -- Ba(OH)$_2$·8H$_2$O. --, therefor.

At column 20, line 37, delete "Ba(OH)$_2$.8H$_2$O." and insert -- Ba(OH)$_2$·8H$_2$O. --, therefor.

At column 21, line 61, delete "Coll." And insert -- Coll --, therefor.

At column 22, line 38 (approx.), after "1974" insert -- . --.

At column 23, line 43, after "1993" insert -- . --.

At column 24, line 50 (approx.), after "1978" insert -- . --

At column 24, line 61, after "2001" insert -- . --.

At column 24, line 65, after "2002" insert -- . --.

At column 25, line 6, delete "Metabol." and insert -- Metabol --, therefor.

At column 25, line 6, after "2002" insert -- . --.

At column 25, line 57, in Claim 7, delete "front" and insert -- from --, therefor.

UNITED STATES PATENT AND TRADEMARK OFFICE
CERTIFICATE OF CORRECTION

PATENT NO.         : 7,144,865 B2
APPLICATION NO. : 10/768200
DATED                 : December 5, 2006
INVENTOR(S)       : Moon K. Song It is certified that error appears in the above-identified patent and that said Letters Patent is hereby corrected as shown below:

At column 26, line 24 (approx.), in Claim 14, delete "mamml" and insert -- mammal --, therefor.

At column 26, line 25 (approx.), in Claim 14, delete "maount" and insert -- amount --, therefor.

At column 26, line 35, in Claim 17, delete "ararhidonic" and insert -- arachidonic --, therefor.

At column 26, line 47 (approx.), in Claim 20, delete "L-hisitidine" and insert -- L-histidine --, therefor.

At column 26, line 47 (approx.) in Claim 20, delete "administed" and insert -- administered --, therefor.

Signed and Sealed this

Fifth Day of June, 2007

JON W. DUDAS
*Director of the United States Patent and Trademark Office*